US012746338B2

(12) United States Patent
Corbett et al.

(10) Patent No.: US 12,746,338 B2
(45) Date of Patent: Sep. 29, 2026

(54) MANAGEMENT PLATFORM FOR INTELLIGENT INJECTION DEVICES

(71) Applicant: DataDose, LLC, Lexington, KY (US)

(72) Inventors: Jeremy Corbett, Nicholasville, KY (US); John Spencer, Lexington, KY (US); Nathaniel Mitchell, Nicholasville, KY (US)

(73) Assignee: DataDose, LLC, Lexington, KY (US)

( * ) Notice: Subject to any disclaimer, the term of this patent is extended or adjusted under 35 U.S.C. 154(b) by 872 days.

(21) Appl. No.: 17/926,157

(22) PCT Filed: May 21, 2021

(86) PCT No.: PCT/US2021/033646
§ 371 (c)(1),
(2) Date: Nov. 18, 2022

(87) PCT Pub. No.: WO2021/237085
PCT Pub. Date: Nov. 25, 2021

(65) Prior Publication Data

US 2023/0191036 A1 Jun. 22, 2023

Related U.S. Application Data

(60) Provisional application No. 63/028,182, filed on May 21, 2020.

(51) Int. Cl.
*A61M 5/31* (2006.01)
*A61M 5/315* (2006.01)
(Continued)

(52) U.S. Cl.
CPC .... *A61M 5/31501* (2013.01); *A61M 5/31568* (2013.01); *G16H 10/60* (2018.01); (Continued)

(58) Field of Classification Search
CPC . A61M 5/20; A61M 5/31568; A61M 5/31511
See application file for complete search history.

(56) References Cited

U.S. PATENT DOCUMENTS 4,950,246 A 8/1990 Muller
7,300,418 B2 11/2007 Zaleski
(Continued)

FOREIGN PATENT DOCUMENTS

CA 3140408 A1 11/2020
EP 3991771 A1 5/2022
(Continued)

OTHER PUBLICATIONS

Non-Final Office Action for U.S. Appl. No. 16/131,749, dated Apr. 1, 2020, 9 pages.
(Continued)

*Primary Examiner* — Courtney Fredrickson
(74) *Attorney, Agent, or Firm* — Michael T. Abramson; Jordan IP Law, LLC

(57) ABSTRACT

A reporting injection device, including a barrel in fluid communication with a needle connected with a first end of the barrel, a piston including a plunger, the piston positioned within a second end of the barrel and the plunger having a fluid-tight interaction with an interior of the barrel, and a microprocessor in electronic communication with a switch and a wireless module, the microprocessor configured to send an administration data from the wireless module after triggering the switch.

16 Claims, 24 Drawing Sheets

(51) Int. Cl.
*G16H 10/60* (2018.01)
*G16H 20/17* (2018.01)
*G16H 40/20* (2018.01)

(52) U.S. Cl.
CPC ............. *G16H 20/17* (2018.01); *G16H 40/20* (2018.01); *A61M 2205/3368* (2013.01); *A61M 2205/3584* (2013.01); *A61M 2205/52* (2013.01)

(56) References Cited

U.S. PATENT DOCUMENTS 9,317,916 B1 4/2016 Hanina et al.
9,623,191 B2 4/2017 Uber et al.
10,825,560 B1 11/2020 Berenson
10,911,515 B2 2/2021 Biasi et al.
11,102,304 B1 8/2021 Jain et al.
11,210,611 B2 12/2021 Kamen et al.
12,260,959 B1 3/2025 Minetti et al.
2001/0047281 A1 11/2001 Keresman, III et al.
2003/0036683 A1 2/2003 Kehr et al.
2003/0110060 A1 6/2003 Clementi
2007/0179453 A1 8/2007 Lim et al.
2007/0219503 A1 9/2007 Loop et al.
2007/0225653 A1 9/2007 Lim et al.
2009/0076338 A1 3/2009 Zdeblick et al.
2011/0009812 A1 1/2011 Brown
2012/0209243 A1 8/2012 Yan
2013/0023813 A1 1/2013 Roorda
2013/0023825 A1* 1/2013 Edwards ............. A61M 5/3202 604/196
2013/0276785 A1 10/2013 Melker et al.
2013/0310756 A1* 11/2013 Whalley ................. A61M 5/24 604/189
2013/0338628 A1 12/2013 Robertson et al.
2014/0074454 A1 3/2014 Brown et al.
2014/0180711 A1 6/2014 Kamen et al.
2014/0207099 A1 7/2014 Nagar et al.
2015/0057611 A1 2/2015 Bureau
2015/0112703 A1* 4/2015 Sysko .................... G16H 40/20 705/2
2015/0174342 A1 6/2015 Mitrosky et al.
2015/0278924 A1 10/2015 Maurer et al.
2016/0012205 A1* 1/2016 Saint ........................ H04B 7/24 604/189
2016/0042154 A1 2/2016 Goldberg et al.
2016/0171597 A1 6/2016 Todeschini
2016/0171777 A1 6/2016 Todeschini et al.
2016/0243318 A1 8/2016 Despa et al.
2016/0259913 A1 9/2016 Yu et al.
2017/0007765 A1* 1/2017 Cowe .................. A61M 5/2033
2017/0076060 A1 3/2017 Pilkington et al.
2017/0095638 A1 4/2017 Young et al.
2017/0119969 A1 5/2017 McCullough et al.
2017/0136185 A1 5/2017 Rios et al.
2017/0146381 A1 5/2017 Eckel et al.
2017/0203030 A1 7/2017 Brewer et al.
2017/0245943 A1 8/2017 Foster et al.
2017/0262604 A1 9/2017 Francois
2017/0325091 A1 11/2017 Freeman et al.
2017/0357775 A1 12/2017 Ekin
2018/0017531 A1* 1/2018 Juhnke ................. G01N 29/343
2018/0085517 A1 3/2018 Laurence et al.
2018/0113985 A1 4/2018 Gandy et al.
2018/0133400 A1 5/2018 Almoumen
2018/0166163 A1 6/2018 Sudharsan
2018/0182491 A1 6/2018 Belliveau et al.
2018/0193564 A1 7/2018 Dahmani
2018/0308569 A1 10/2018 Luellen
2018/0333543 A1 11/2018 Diaz et al.
2018/0369488 A1 12/2018 Carlsson et al.
2019/0054247 A1* 2/2019 Dantsker ........... A61M 5/31553
2019/0060577 A1* 2/2019 Vallis ...................... G01B 7/003
2019/0130792 A1 5/2019 Rios et al.
2019/0209777 A1* 7/2019 O'Connell ......... A63B 24/0062
2019/0247050 A1 8/2019 Goldsmith
2019/0262534 A1 8/2019 Agard et al.
2019/0282761 A1 9/2019 Wilson et al.
2020/0016331 A1* 1/2020 Lee ................... A61M 5/14546
2020/0061301 A1 2/2020 Hatamian et al.
2020/0082327 A1 3/2020 Arefieg
2020/0086046 A1 3/2020 Corbett et al.
2020/0093993 A1 3/2020 O'Rourke et al.
2020/0139053 A1* 5/2020 Faught .............. A61M 5/31568
2020/0226951 A1 7/2020 Rios et al.
2020/0289751 A1 9/2020 Despa et al.
2020/0303047 A1 9/2020 Bostic et al.
2020/0350052 A1 11/2020 Saint et al.
2020/0364801 A1 11/2020 Basra
2020/0390596 A1 12/2020 Chalberg, Jr. et al.
2021/0008294 A1 1/2021 Gentz
2021/0060246 A1 3/2021 Weydt et al.
2021/0217516 A1 7/2021 Nash et al.
2021/0260289 A1 8/2021 Kamath et al.
2021/0288950 A1 9/2021 Rodriguez Bravo et al.
2022/0023391 A1 1/2022 Michelich et al.
2022/0031956 A1 2/2022 Helmer
2022/0051778 A1 2/2022 Kühni et al.
2022/0183915 A1 6/2022 Augustine et al.
2022/0301681 A1 9/2022 Coetzee
2022/0336074 A1 10/2022 Bakos et al.
2023/0081577 A1 3/2023 Walker et al.
2023/0191036 A1 6/2023 Corbett et al.
2023/0298723 A1 9/2023 Mercolino et al.
2023/0302224 A1 9/2023 Prince et al.
2023/0330328 A1 10/2023 Moberg et al.
2023/0368226 A1 11/2023 Mestres et al.
2023/0386677 A1 11/2023 Ferro et al.
2023/0414432 A1 12/2023 Augustine et al.
2023/0414433 A1 12/2023 Augustine et al.
2024/0157045 A1 5/2024 Kostal et al.
2024/0232031 A1 7/2024 Kang et al.
2024/0285956 A1 8/2024 Forsell
2025/0000453 A1 1/2025 Lettman et al.
2025/0050014 A1 2/2025 Shin et al.
2025/0054615 A1 2/2025 Ronen et al.
2025/0329451 A1 10/2025 Minetti et al.
2026/0079511 A1 3/2026 Roychoudhury et al.

FOREIGN PATENT DOCUMENTS

WO 2006060572 A1 6/2006
WO 2016210404 A1 12/2016
WO 2017156523 A1 9/2017
WO 2018009509 A2 1/2018
WO 2018106475 A1 6/2018
WO 2020236481 A1 11/2020
WO 2021237085 A1 11/2021

OTHER PUBLICATIONS

Final Office Action for U.S. Appl. No. 16/131,749, dated Oct. 1, 2020, 11 pages.
Non-Final Office Action for U.S. Appl. No. 16/131,749, dated Mar. 2, 2021, 13 pages.
Non-Final Office Action for U.S. Appl. No. 16/131,749, dated Sep. 16, 2021, 10 pages.
Notice of Allowance for U.S. Appl. No. 16/131,749, dated Jan. 13, 2022, 7 pages.
Non-Final Office Action for U.S. Appl. No. 17/724,177, dated Apr. 11, 2024, 11 pages.
Final Office Action for U.S. Appl. No. 17/724,177, dated Oct. 22, 2024, 13 pages.
Non-Final Office Action for U.S. Appl. No. 17/724,177 dated Apr. 21, 2025, 9 pages.
Restriction Requirement Office Action for U.S. Appl. No. 19/031,780 dated May 19, 2025, 6 pages.
Restriction Requirement Office Action for U.S. Appl. No. 19/031,836 dated Apr. 25, 2025, 6 pages.
Non-Final Office Action for U.S. Appl. No. 19/031,836 dated Jul. 18, 2025, 17 pages.

(56) References Cited

OTHER PUBLICATIONS

Restriction Requirement Office Action for U.S. Appl. No. 19/031,854 dated May 9, 2025, 6 pages.
Restriction Requirement Office Action for U.S. Appl. No. 19/031,862 dated May 9, 2025, 6 pages.
Non-Final Office Action for U.S. Appl. No. 19/031,940 dated Apr. 11, 2025, 25 pages.
Final Office Action for U.S. Appl. No. 19/031,940 dated Jul. 3, 2025, 13 pages.
Examination Report dated Nov. 17, 2025 for European Application No. 21808546.2, 5 pages.
Final Office Action for U.S. Appl. No. 19/031,836 dated Nov. 26, 2025, 26 pages.
Non-Final Office Action for U.S. Appl. No. 19/280,969 dated Dec. 1, 2025, 38 pages.
Non-Final Office Action for U.S. Appl. No. 19/281,013 dated Dec. 11, 2025, 35 pages.
Non-Final Office Action for U.S. Appl. No. 19/281,035 dated Dec. 11, 2025, 29 pages.
International Search Report and Written Opinion of International Searching Authority with mailing dates of Oct. 20, 2021 for International Application No. PCT/US2021/033646.
Notice of Allowance for U.S. Appl. No. 19/031,854 dated Jul. 28, 2025, 32 pages.
Notice of Allowance for U.S. Appl. No. 19/031,862 dated Jul. 29, 2025, 43 pages.
Non-Final Office Action for U.S. Appl. No. 19/031,780 dated Aug. 6, 2025, 30 pages.
Notice of Allowance for U.S. Appl. No. 19/031,940 dated Oct. 17, 2025, 21 pages.
Final Office Action for U.S. Appl. No. 17/724,177, dated Oct. 29, 2025, 32 pages.
Extended European Search Report dated May 23, 2024 for European Application No. 21808546.2.
Notice of Allowance for U.S. Appl. No. 19/031,780 dated Dec. 29, 2025, 20 pages.
Non-Final Office Action or U.S. Appl. No. 19/314,966 dated Dec. 31, 2025, 42 pages.
Notice of Allowance for U.S. Appl. No. 19/315,011 dated Jan. 7, 2026, 39 pages.
Notice of Allowance for U.S. Appl. No. 19/314,936 dated Jan. 13, 2026, 30 pages.
Notice of Allowance for U.S. Appl. No. 17/724,177 dated Jan. 13, 2026, 12 pages.
Notice of Allowance for U.S. Appl. No. 19/031,881 dated Jan. 14, 2026, 49 pages.
Notice of Allowance for U.S. Appl. No. 19/315,027 dated Feb. 6, 2026, 37 pages.
Notice of Allowance for U.S. Appl. No. 19/031,780 dated Feb. 27, 2026, 26 pages.
Final Office Action for U.S. Appl. No. 19/280,969 dated Mar. 4, 2026, 38 pages.
Notice of Allowance for U.S. Appl. No. 17/724,177 dated Mar. 10, 2026, 25 pages.
Non-Final Office Action for U.S. Appl. No. 19/031,870 dated Mar. 25, 2026, 52 pages.
Notice of Allowance for U.S. Appl. No. 19/314,864 dated Mar. 27, 2026, 45 pages.
Final Office Action for U.S. Appl. No. 19/281,013 dated Mar. 30, 2026, 29 pages.
Final Office Action for U.S. Appl. No. 19/281,035 dated Mar. 30, 2026, 32 pages.
Non-Final Office Action for U.S. Appl. No. 19/031,928 dated Apr. 7, 2026, 53 pages.
Notice of Allowance for U.S. Appl. No. 19/315,011 dated Apr. 7, 2026, 15 pages.
Notice of Allowance for U.S. Appl. No. 19/031,940 dated Apr. 8, 2026, 28 pages.
Notice of Allowance for U.S. Appl. No. 17/724,177 dated Apr. 9, 2026, 16 pages.
Notice of Allowance for U.S. Appl. No. 19/031,780 dated Apr. 9, 2026, 17 pages.
Notice of Allowance for U.S. Appl. No. 19/314,936 dated Apr. 10, 2026, 15 pages.
Notice of Allowance for U.S. Appl. No. 19/031,881 dated Apr. 15, 2026, 22 pages.
Notice of Allowance for U.S. Appl. No. 19/031,836 dated Apr. 17, 2026, 23 pages.
Mahzabin, Rahnuma et al. "Blockchain associated machine learning and loT based hypoglycemia detection system with auto-injection feature", Indonesian Journal of Electrical Engineering and Computer Science, vol. 27, No. 1, Jul. 2022, ISSN: 2502-4752, DOI: 10.11591/ijeecs.v27.il.pp447-455.
Non-Final Office Action for U.S. Appl. No. 19/031,911 dated Apr. 20, 2026, 55 pages.
Final Office Action for U.S. Appl. No. 19/314,966 dated Apr. 20, 2026, 24 pages.
Non-Final Office Action for U.S. Appl. No. 19/031,890 dated Apr. 21, 2026, 53 pages.
Notice of Allowance for U.S. Appl. No. 19/451,171 dated Apr. 22, 2026, 37 pages.
Notice of Allowance for U.S. Appl. No. 19/451,472 mailed May 13, 2026, 48 pages.
International Search Report and Written Opinion for PCT Application No. PCT/US2025/053140 mailed Jun. 10, 2026, 39 pages.
Faisal S, Samoth D, Aslam Y, Patel H, Park S, Baby B, Patel T. Key Features of Smart Medication Adherence Products: Updated Scoping Review. JMIR Aging. Dec. 19, 2023;6:e50990. doi: 10.2196/50990. PMID: 38113067; PMCID: PMC10762620 (Year: 2023).

* cited by examiner

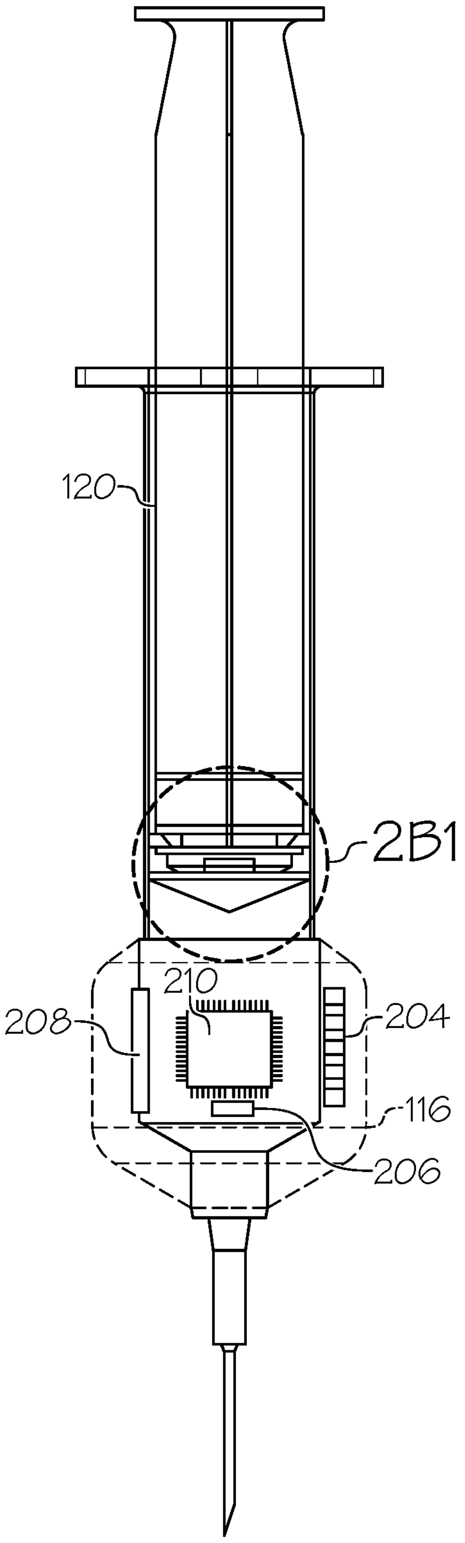
FIG. 2B
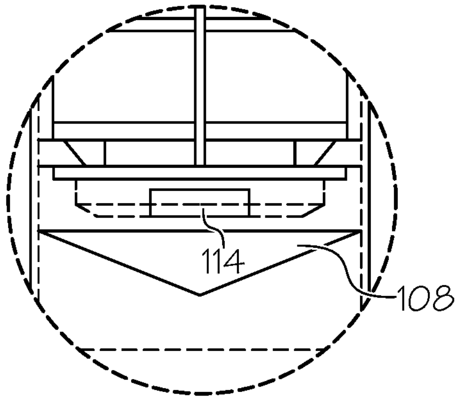
FIG. 2B1

MANAGEMENT PLATFORM FOR INTELLIGENT INJECTION DEVICES

CROSS-REFERENCE TO RELATED APPLICATIONS

This application claims priority to U.S. provisional application No. 63/028,182, filed on May 21, 2020, and entitled MANAGEMENT PLATFORM FOR INTELLIGENT INJECTION DEVICES, which is hereby incorporated by reference as if fully set forth herein in its entirety.

FIELD

The present disclosure relates generally to a management platform for injection devices, such as syringes, and, more particularly, to data reporting regarding administration completion of an injectable pharmaceutical.

BACKGROUND

Understanding administration of drugs and their interaction in the healthcare ecosystem are important in delivering beneficial patient care. Applicant appreciates that regular pharmaceutical therapy and a need for real time data management related to both timing of and compliance in dosing bundled with increased information sharing across the care continuum can provide valuable insight for improving care and, in turn, reducing fraud, waste, and abuse.

SUMMARY

According to some embodiments of the present disclosure, an intelligent injection device is disclosed.

The intelligent injection device may include a barrel in fluid communication with a needle connected with a first end of the barrel, a piston including a plunger, the piston positioned within a second end of the barrel and the plunger having a fluid-tight interaction with an interior of the barrel, and a microprocessor in electronic communication with a switch and a wireless module, the microprocessor configured to send an administration data from the wireless module after triggering the switch.

In some embodiments, the intelligent injection device may include a barrel in fluid communication with a needle connected with a first end of the barrel, a piston including a plunger, the piston positioned within a second end of the barrel and the plunger having a fluid-tight interaction with an interior of the barrel, and a microprocessor in electronic communication with a temperature sensor and a locking mechanism engaged with a stalk of the piston to prevent injection.

According to some embodiments of the present disclosure, a method of reporting patient compliance is disclosed. The method may include generating, by an injection device including reporting components, an administration data including a binary administration completion flag, and sending the administration data.

According to some embodiments of the present disclosure, an intelligent injection device for injection of a pharmaceutical into a patient may comprise a barrel having an interior for holding pharmaceutical, the barrel further having a first end and a second end, a needle in fluid communication with the barrel and connected with the first end of the barrel, a piston positioned within the second end of the barrel, the piston including a plunger having a fluid-tight interaction with the interior of the barrel, and a mechanical switch disposed on the piston and configured to close upon injection of said pharmaceutical into said patient. The intelligent injection device may include a wireless module configured to transmit data, and a microprocessor in electrical communication with the mechanical switch and the wireless module, wherein the microprocessor is configured to transmit administration data related to injection of said pharmaceutical via the wireless module in response to closing of the mechanical switch.

According to some embodiments of the present disclosure, an intelligent injection device may comprise a temperature sensor in electrical communication with the microprocessor and may be configured to sense a temperature of said pharmaceutical and transmit temperature data to the microprocessor indicative of the temperature of said pharmaceutical, and include a locking mechanism engaged with the piston that is in electrical communication with the microprocessor, wherein the microprocessor may be configured to transmit a locking signal to the locking mechanism, and the locking mechanism may be configured to lock the piston in response to receiving the locking signal.

In embodiments, an intelligent injection device, according to the present disclosure, may comprise a load sensor in electrical communication with the microprocessor and be configured to sense force caused by depression of the plunger and transmit force data to the microprocessor indicative of force caused by depression of the plunger.

In embodiments, an intelligent injection device, according to the present disclosure, may comprise an amount sensor in electrical communication with the microprocessor and be configured to sense an amount of said pharmaceutical injected into said patient upon depression of the plunger and transmit pharmaceutical amount data to the microprocessor indicative of said amount of said pharmaceutical injected into said patient upon depression of the plunger.

In embodiments, an intelligent injection device, according to the present disclosure, may comprise a damage sensor in electrical communication with the microprocessor and be configured to sense damage to the intelligent injection device and transmit damage data to the microprocessor indicative of damage to the intelligent injection device.

In embodiments, an intelligent injection device, according to the present disclosure, may comprise an automatic injection system configured to facilitate automatic delivery of said pharmaceutical by the intelligent injection device into said patient According to some embodiments of the present disclosure, methods are provided for determining compliance of an injection event, based at least in part by receiving an administration datum, relating to an injection event, from a wireless module associated with an intelligent injection device, by a server of an injectable administration compliance management platform, determining a treatment schedule with which the injection event is associated, wherein the treatment schedule is stored in a database associated with the injectable administration compliance management platform, using the administration datum, by an artificial intelligence module of the injectable administration compliance management platform, to calculate a compliance score for the injection event, wherein the compliance score is based at least in part on a conformance of the administration datum to at least one criterion of the treatment schedule, comparing the compliance score to a compliance threshold metric to categorize the injection event as compliant, non-compliant or indeterminate, wherein the compliance threshold metric is a quantitative requirement of the treatment schedule, generating a message summarizing the categorization of the injection event using an alerts module of the injectable administration compliance management platform, and sending the message to a party associated with the treatment schedule.

In embodiments, according to the present disclosure, an administration datum may be a plurality of administration data relating to the injection event, wherein the plurality of administration data may include at least data relating to a substance type within the intelligent injection device and data relating to usage of the intelligent injection device. An administration datum may relate to a substance amount ejected from the intelligent injection device, to a duration of substance release from the intelligent injection device, to a temperature of a substance within the intelligent injection device, to a substance identifier of a substance within the intelligent injection device, or some other characteristic.

In embodiments, according to the present disclosure, a treatment schedule may be stored on the intelligent injection device. A treatment schedule may include dosage requirements for a substance to be administered using the intelligent injection device, injection timing requirements for a substance to be administered using the intelligent injection device, or some other treatment information.

In embodiments, according to the present disclosure, a compliance score may be stored in an electronic medical record.

In embodiments, according to the present disclosure, a compliance threshold metric may be obtained from a source external to the injectable administration compliance management platform.

In embodiments, according to the present disclosure, a party associated with the treatment schedule may be a healthcare provider, an electronic medical record, a healthcare reimbursement entity, or some other party.

A more complete understanding of the disclosure will be appreciated from the description and accompanying drawings and the claims, which follow.

BRIEF DESCRIPTION OF THE DRAWINGS

The accompanying drawings, which are included to provide a better understanding of the disclosure, illustrate embodiment(s) of the disclosure and together with the description serve to explain the principle of the disclosure. In the drawings:

FIG. 2B is a diagram that illustrates the reporting components of the reporting injection device according to some embodiments of the present disclosure.

FIG. 2B1 is a diagram that illustrates a zoomed-in partial view of the reporting components of the reporting injection device of FIG. 2B.

DETAILED DESCRIPTION

The present disclosure relates generally to injection devices, such as syringes, and, more particularly, to data reporting regarding administration completion of an injectable pharmaceutical.

Embodiments of the present disclosure may bring novel biologics compliance to the market for the first time. Insurers, employers, health care providers, and loved ones may benefit when patient care plans receive a monocular focus on quality and completion. Embodiments of the present disclosure may provide those with acute and chronic conditions in need of regular pharmaceutical therapy, such as an ongoing course of life-saving injectable drugs, with real-time data management related to both timing of and compliance in dosing. Information shared across the care continuum may provide valuable insight into how and when providers should intervene, and may further eliminate fraud, waste, and abuse within this expensive space. Embodiments of the present disclosure may drive compliance, illuminate opportunities for intervention, and save money in the pharmaceutical space with a great need for innovation and within a population that deserves the best care available. For example, many biologics may have a high cost per injection. The Humira™, Enbrel™, and/or Remicade™ biologics may be used as an immunosuppressant to treat autoimmunity. These biologics may be expensive. For example, the Humira™ biologic may cost up to $5,000 per injection. Furthermore, the biologics may be temperature sensitive. The Humira™ and Enbrel™ biologics may be recommended to be stored between 2 and 8 degrees Celsius, without freezing, and may be kept at room temperature for up to 14 days. Such a temperature range corresponding to the temperature tolerance of a pharmaceutical may be referred to as a predetermined temperature range. The time period that a pharmaceutical may exceed the predetermined temperature range may be referred to as a time tolerance. Regarding some pharmaceuticals, such as biologics, the time tolerance may exclude freezing. The Remicade™ biologic may be recommended to be stored between 2 and 8 degrees Celsius, without freezing, and may be kept at room temperature for 24 hours. Due to the sensitivity of these biologics, a pharmacist may refuse inventory shipments where cold chain storage has been broken. These biologics may be shipped preloaded into injection devices.

Figure 1A:
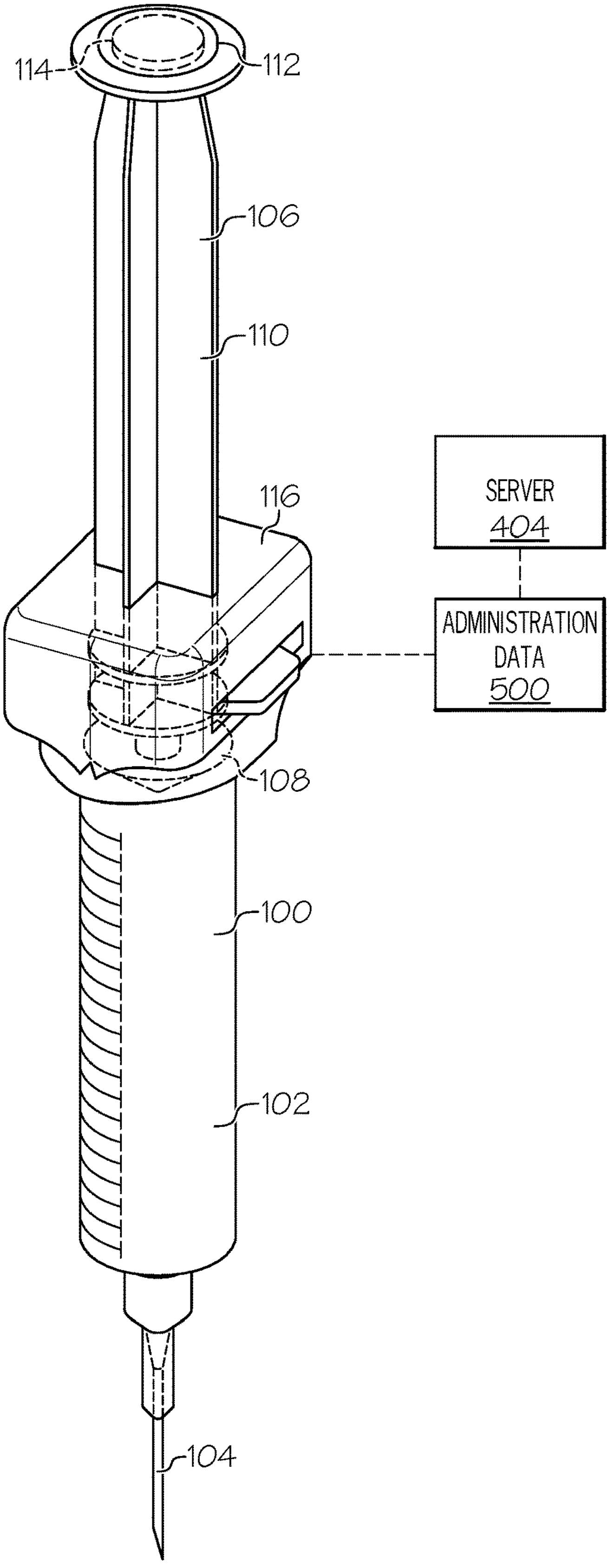
FIG. 1A is a diagram that illustrates a reporting injection device according to some embodiments of the present disclosure.

FIG. 1A illustrates embodiments of an injection device 100. The injection device 100 may include a barrel 102 having a first end and a second end. The barrel 102 may be sized to receive and/or store a fluid, such as a pharmaceutical, a medication, a biologic, or any other suitable fluid. With respect to diabetes management, the barrel 102 may be sized to retain sufficient insulin for one prescribed administration. The injection device may include a needle 104 connected with the first end of the barrel and in fluid communication with the barrel 102 for injecting pharmaceutical into the patient. The needle 104 may define a hollow conduit through which the pharmaceutical may be transported from the barrel 102 through the needle 104 and into the patient.

The injection device 100 may include a piston 106 for driving the pharmaceutical during injection. The piston 106 includes a plunger 108, a stalk 110, and a head 112. The plunger 108 may be positioned within the second end of the barrel 102 and may engage the inside of the barrel 102 such that a seal is created, the seal being sufficient to push retained pharmaceutical from the barrel 102 through the needle 104. The plunger 108 may be connected to the stalk 110. The stalk 110 may be connected to the head 112. The plunger 108 may be driven through the barrel 102 by operation of pressing the head 112 toward the barrel. The plunger may be at least partially composed of rubber, plastic, or any other material sufficient to maintain a fluid-tight interaction between the plunger 108 and an interior of the barrel 102 such that pharmaceutical is administered as the piston 106 is compressed. The stalk 110 may have sufficient length to drive the plunger 108 to a distal end of the barrel 102. In this manner, some, most, or all of the pharmaceutical may be driven out of the barrel 102.

In some embodiments, the head 112 may include a magnet 114. The magnet 114 may be a neodymium magnet or other magnet sufficient to induce a magnetic field onto reporting components 116 when the head 112 is completely pressed to the casing of the reporting components 116. When the magnetic field is induced onto the reporting components 116, the reporting components 116 may send administration data 500 to a server 404 over an internet connection (e.g., wireless, cellular data, etc.). In some embodiments, the magnetic field may be induced onto the reporting components 116 when the head 112 is almost completely pressed to the casing of the reporting components 116, such as when the injection administration is effectively complete (e.g., when the head 112 is 98% compressed or other predetermined and/or reconfigurable values).

In some embodiments, a mechanical switch may be used to indicate that the injection has been administered by compressing the switch when the head 112 is completely (or almost completely) pressed to the casing of the reporting components 116 or to an end of the barrel 102. In these embodiments, a reporting circuit may be completed or broken. Detection of this change in the circuit may, in embodiments, allow for a microprocessor 210 (FIG. 2A) in the reporting components 116 to alter the administration data 500 to reflect a completed injection.

Figure 1B:
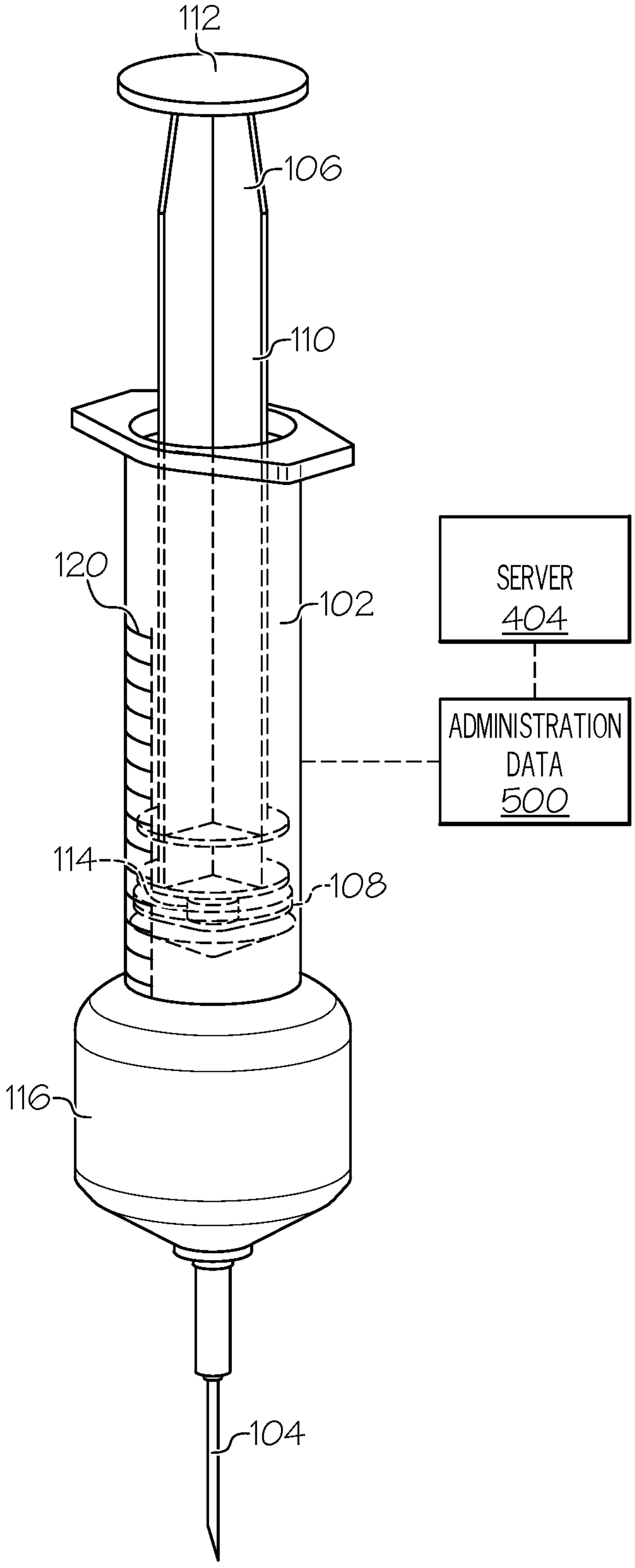
FIG. 1B is a diagram that illustrates a reporting injection device of having an alternate arrangement of reporting components according to some embodiments of the present disclosure.

FIG. 1B illustrates other embodiments of the injection device 100. By way of these examples, the magnet 114 may be positioned in the plunger 108. The reporting components 116 may be positioned at the end of the barrel 102 proximate the needle 104.

Figure 2A:
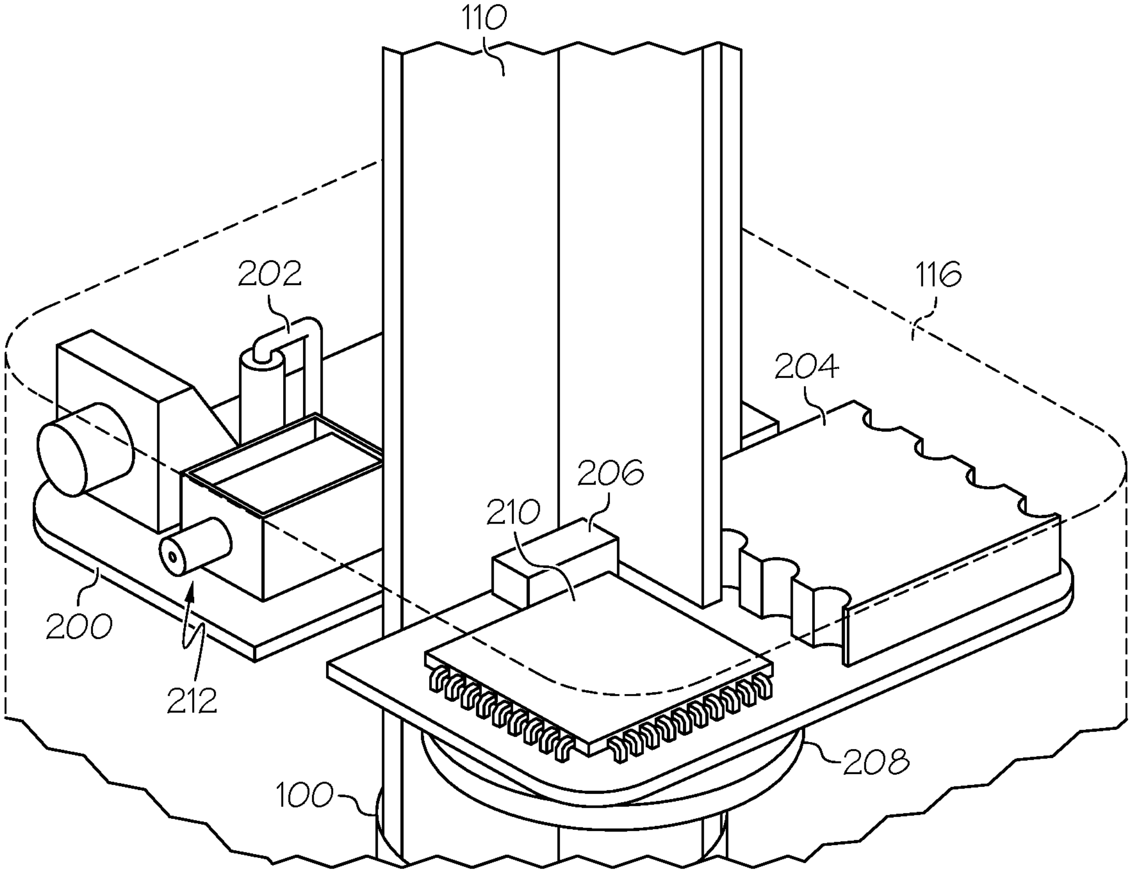
FIG. 2A is a diagram that illustrates reporting components of the injection device according to some embodiments of the present disclosure.

FIG. 2A illustrates embodiments of the injection device 100 including the reporting components 116 of the injection device 100. For example, the reporting components 116 may include a temperature sensor 202, a wireless module 204, a switch 206, a battery 208, a microprocessor 210, and/or a locking mechanism 212.

The battery 208 may be a coin cell battery or any other battery sufficient to power the reporting components 116. Coin cell batteries may provide a stable output voltage until the end of the life of the battery. Coin cell battery capacities may range from 150 to 200 mAh and voltage characteristics may range from gradually reducing to fairly constant. Some coin cell batteries may be specified for a continuous low drain with a high pulse on demand.

The temperature sensor 202 may be or include any suitable device for measuring temperature and providing an electronic measurement to the microprocessor 210. Examples of suitable devices include a thermistor, a resistance temperature detector, a thermocouple, and/or a semiconductor-based sensor. In some embodiments, the temperature sensor 202 may be positioned on a circuit board of the reporting components 116. The temperature sensor 202 may be configured to measure the temperature ambient to the injection device 100, such as by measuring the temperature of the air around the reporting components 116. However, embodiments may include a temperature probe within the barrel 102 in order to measure the temperature of the pharmaceutical.

A thermistor may include a thermally sensitive resistor that may exhibit a large, predictable, and precise change in resistance correlated to variations in temperature. A negative temperature coefficient (NTC) thermistor provides a very high resistance at low temperatures. As temperature increases, the resistance may decrease. Because an NTC thermistor may experience a large change in resistance per ° C., small changes in temperature may be reflected quickly and with high accuracy (0.05 to 1.5° C.). Because of its exponential nature, the output of an NTC thermistor may require linearization. The effective operating range may be −50 to 250° C. for gas encapsulated thermistors or 150° C. for standard.

A resistance temperature detector (RTD), also known as a resistance thermometer, may measure temperature by correlating the resistance of the RTD element with temperature. An RTD may consist of a film or, for greater accuracy, a wire wrapped around a ceramic or glass core. The most accurate RTDs may be made using platinum. However, lower-cost RTDs can be made from nickel or copper, at a cost to accuracy. Platinum RTDs offer a fairly linear output that may be highly accurate (0.1 to 1° C.) across −200 to 600° C.

A thermocouple may consist of two wires of different metals connected at two points. The varying voltage between these two points may reflect proportional changes in temperature. The thermocouple may be non-linear, requiring conversion when used for temperature control and compensation. However, conversion can be accomplished using a lookup table. Accuracy may be relatively low, from 0.5 to 5° C. However, thermocouples may operate across the widest temperature range, from −200 to 1750° C.

In some embodiments, the temperature sensor 202 may be placed on an integrated circuit (IC). The temperature sensor may include two identical diodes with temperature-sensitive voltage vs current characteristics that can be used to monitor changes in temperature. The diodes of the temperature sensor 202 may offer a linear response.

In some embodiments, the wireless module 204 may be placed on the circuit board 200 such that the wireless module 204 may be in electrical communication with the microprocessor 210 and the battery 208. The wireless module 204 may include a Bluetooth interface, a Bluetooth low energy interface, a Wi-Fi interface, an infrared interface, a cellular interface (e.g., a fixed area transceiver), a near field communication (NFC) interface, a radio-frequency identification (RFID) interface, or any other suitable communication interface.

In some embodiments, the wireless module 204 may be configured to connect to the internet, a computer, and/or a mobile phone. For example, the wireless module 204 may connect directly or indirectly to a local router, modem, server, transmitter tower such as a radio tower, satellite and/or any other gateway to the worldwide web. In some embodiments, the wireless module 204 may be wirelessly connected directly to another computer or handheld device, such as a phone, watch, or tablet. In some embodiments, the wireless module 204 may engage in electronic communication with another computer or device by infrared (IR) transmitter and receiver, Bluetooth connection, fiber optic connection, cellular or mobile network (e.g., fixed area transceivers), or any other connector for transferring electronic data. For example, the wireless module 204 may send data over Bluetooth connection to a computer, server, or other devices. The server 404 may then upload the data for access via an internet connection. The wireless module 204 may transmit data via analog or digital signal, UDP or TCP, http, https, ssh, ftp, sftp, etc., or any other protocol or means to transfer electronic data.

The switch 206 may be a magnetic and/or electrical switch, such as a reed switch. The switch 206 may be positioned on the circuit board 200. The switch 206 may be in electrical communication with the microprocessor 210, the locking mechanism 212, and/or any other reporting components 116. A reed switch may be operated by an applied magnetic field. The reed switch may include a pair of contacts on ferromagnetic metal reeds in a hermetically sealed glass envelope. The contacts may be normally open, closing when a magnetic field is present, or normally closed and opening when a magnetic field is applied. The reed switch may be actuated by a coil, making a reed relay, or by bringing a magnet near to the switch. Once the magnet is pulled away from the switch, the reed switch may go back to its original position. In this manner, the switch 206 may be actuated by application of the magnetic field of the magnet 114, such as when the piston 106 is compressed upon administering an injection or bolus of a pharmaceutical from the barrel 102.

The locking mechanism 212 may be positioned on the circuit board 200. In this manner, the locking mechanism 212 may be in electrical communication with the other components on the circuit board 200, such as the wireless module 204 and/or the microprocessor 210. The locking mechanism 212 may prevent injection of the pharmaceutical by interaction with the stalk 110, when in the locked position. However, the locking mechanism 212 may be switched to an unlocked position, wherein the locking mechanism 212 no longer interacts with the stalk 110. Thereby, the piston 106 may be compressible to allow an injection when the locking mechanism 212 is in the unlocked position.

In some embodiments, the locking mechanism 212 may engage the locked position upon filling the barrel with a prescribed amount or bolus of a pharmaceutical. The locking mechanism 212 may remain in the locked position until predetermined conditions are met. For example, the locking mechanism 212 may remain in the locked position until the microprocessor 210 verifies a user connection between the wireless module 204 and a user device, such as an app on a mobile device. In some embodiments, the locking mechanism 212 may switch to the unlocked position upon meeting one or more, or all, of the predetermined conditions.

An example may include sensing that an injection physically occurs within a patient, such as by a load sensor.

The microprocessor 210 may be positioned on the circuit board 200. In this manner, microprocessor 210 may be in electrical communication with the other components on the circuit board 200, such as the temperature sensor 202, the wireless module 204, the switch 206, the battery 208, and/or the locking mechanism 212.

FIG. 2B illustrates the reporting components 116 of the reporting injection device 100.

Figure 2C:
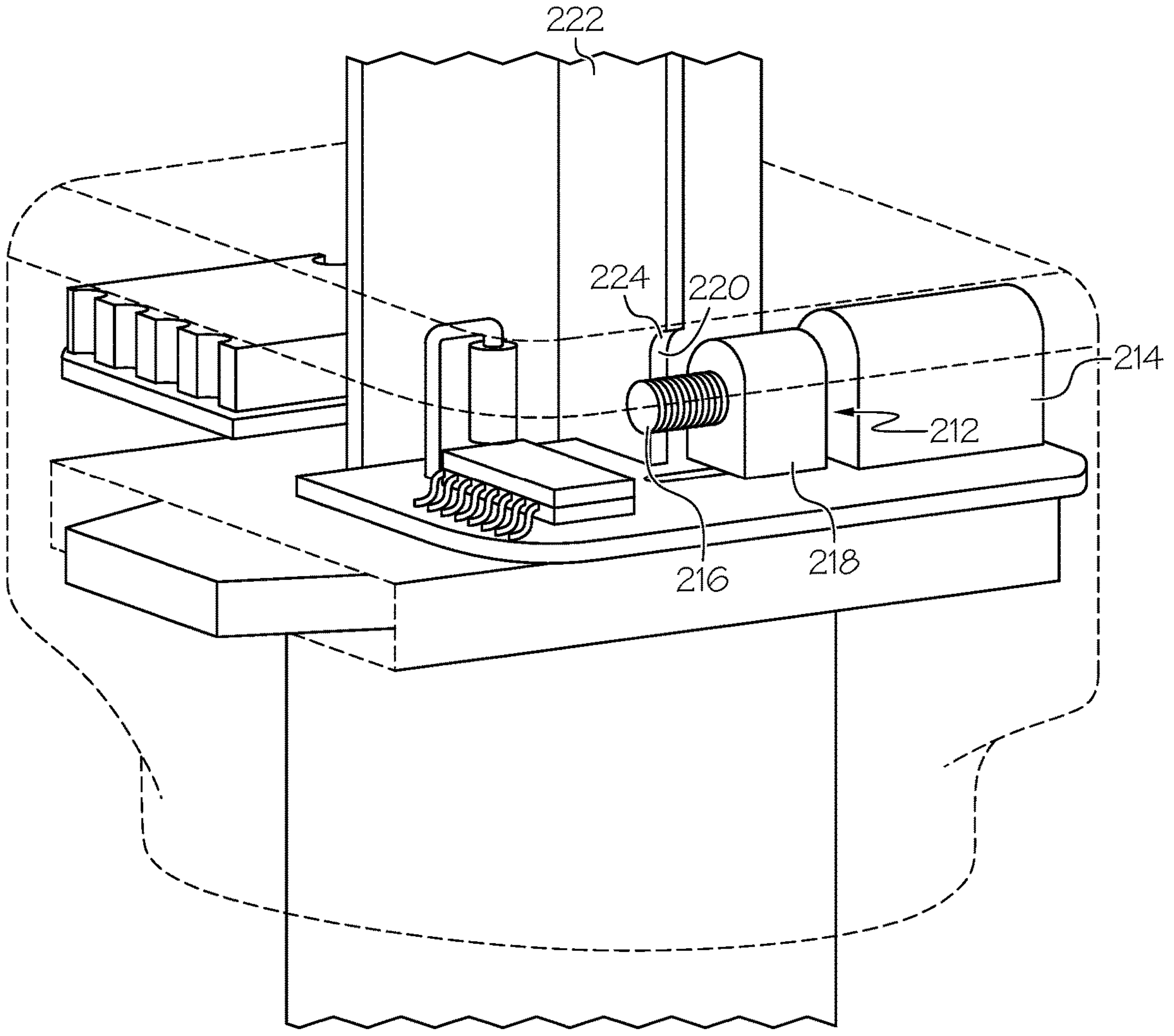
FIG. 2C is a diagram that illustrates a locking mechanism of the reporting components of the reporting injection device with the locking mechanism disengaged according to some embodiments of the present disclosure.

FIG. 2C illustrates the locking mechanism 212 of the reporting components 116 with the locking mechanism 212 disengaged.

The locking mechanism 212 may include a stepper motor, such as micro stepper motor 214. The micro stepper motor 214 may be in rotary communication with a screw 216 such that rotation of the micro stepper motor 214 may rotate the screw 216. A slider block 218 may be disposed on the screw 216 such that rotation of the screw 216 may alter the linear displacement of the slider block 218. For example, the slider block 218 may include threads that interact with the threads of the screw 216 such that rotation of the screw 216 in a first direction may move the slider block 218 proximally to the micro stepper motor 214 and rotation of the screw in a second direction may move the slider block 218 distally from the micro stepper motor 214.

The locking mechanism 212 may further include a slider block receiver 220. The slider block receiver 220 may be integrally formed with the plunger 108 such that a plunger wall 222 of the plunger 108 includes a flange 224 configured to contact the slider block 218 when the slider block 218 is positioned under the flange 224. In some embodiments, the flange 224 may not necessarily contact anything when the slider block 218 is not positioned under the flange 224, such that the plunger wall 222 may pass the slider block 218 and the injection device 100 may be compressed.

Figure 2D:
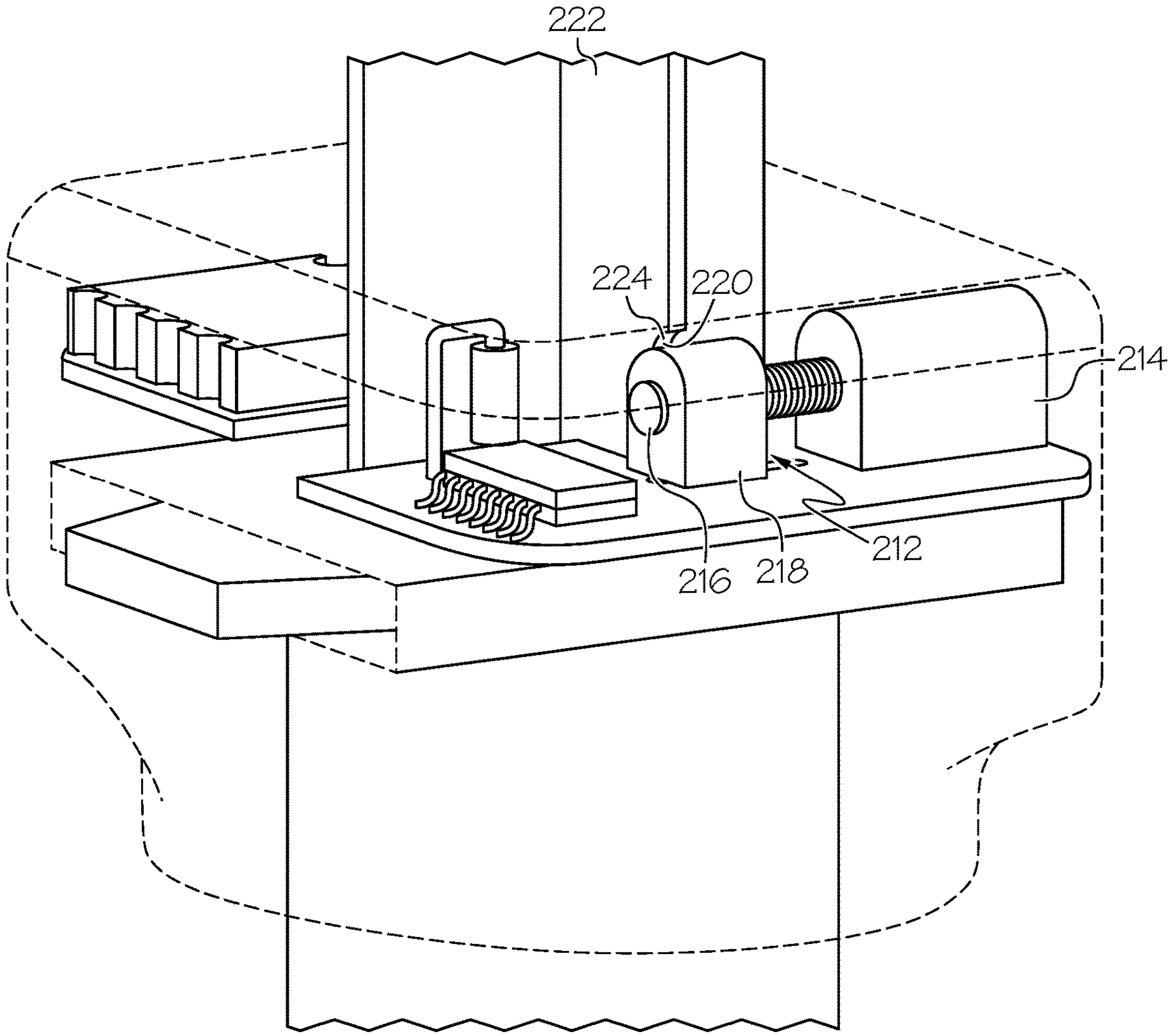
FIG. 2D is a diagram that illustrates the locking mechanism of the reporting components of the reporting injection device with the locking mechanism engaged according to some embodiments of the present disclosure.

FIG. 2D illustrates the locking mechanism 212 of the reporting components 116 of the reporting injection device 100 with the locking mechanism 212 engaged. While the locking mechanism 212 is engaged, the flange 224 may contact the slider block 218. Because the flange 224 and/or the plunger wall 222 will not pass through the slider block 218, the injection device 100 is prevented from compression and/or injection when the locking mechanism 212 is engaged.

In some embodiments, locking and/or unlocking the injection device 100, i.e., engaging or disengaging the locking mechanism 212, may be determined by the disposition of the axis of the screw 216 through the plane of the plunger wall 222 such that flange 224 is or is not capable of contacting the screw 216 and is not or is capable of contacting the slider block 218 when the slider block 218 is positioned under the flange 224. In some embodiments, the plunger wall 222 may define a mortise and the flange 224 may contact the slider block 218 (e.g., as a tenon) to prevent injection when the slider block 218 is positioned in the mortise.

The injection device may include any other suitable locking mechanism.

Figure 2E:
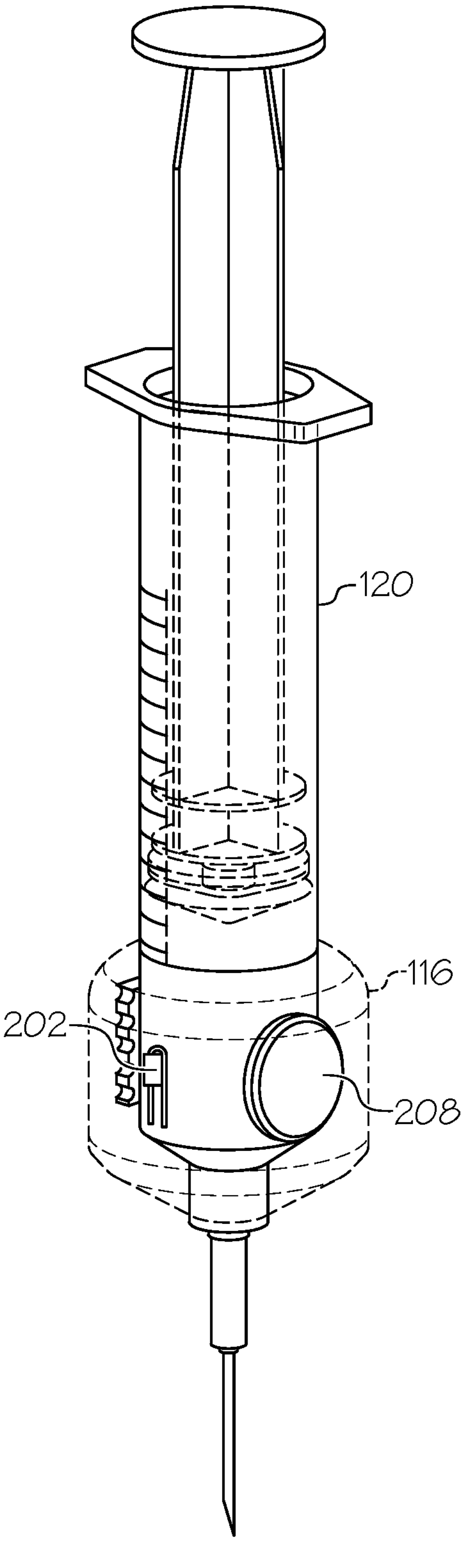
FIG. 2E is a diagram that illustrates an alternate view of the reporting components according to some embodiments of the present disclosure.

FIG. 2E illustrates other embodiments of the reporting components 116. In some embodiments, the injection device 100 includes the reporting components 116 that do not necessarily include the locking mechanism 212. The sensor 202 may detect the proximity of the magnet 114 in the plunger 108 when an injection is completely administered. The microprocessor 210 may record the injection administration completion event and may send the administration data 500 over the wireless module 204.

Figure 3:
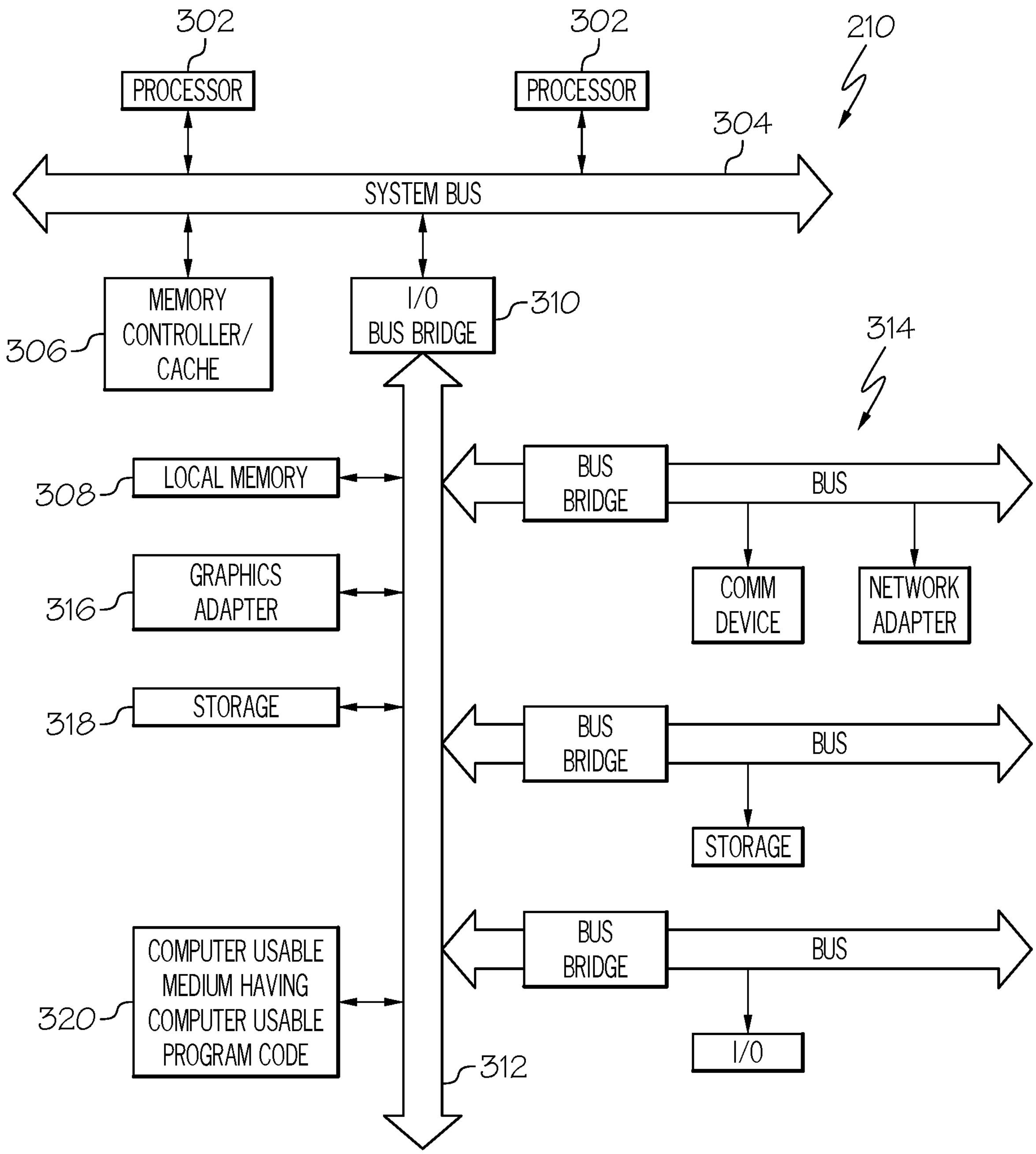
FIG. 3 is a diagram that illustrates a microprocessor of the injection device according to some embodiments of the present disclosure.

FIG. 3 illustrates embodiments of a block-level diagram of the microprocessor 210 of the injection device 100. The microprocessor 210 may be any device capable of sending and receiving electronic data over an interface. For example, a microprocessor or a computer could be used. The microprocessor 210 may also perform operations on and/or modify the data it receives.

The microprocessor 210 may be embodied as hardware circuits or may be software embodiments wherein program code, such as java, C++, etc., manipulates the hardware of a general-purpose hardware circuit. Software embodiments may be implemented as low-level code or even as high-level code operating within an operating system, such as Unix, BSD, Microsoft Windows, iOS, etc.

The microprocessor 210 may include a processing unit (CPU) 302, a local memory 308, a plurality of peripherals and interfaces, and a general-purpose input/output (I/O) interface. The CPU 302 may include local storage. The local storage may be used to store variables, constants, etc. for complex calculations. The local memory 308 may interface with the CPU via a memory interface. The memory interface may allow the CPU to store calculated values, variables, constants, or any other important electronic signal onto physical local memory. The memory interface may include one or more direct memory access controllers. Part or all of the local memory 308 may be committed to program storage, in which data relevant to the operation of the program is stored. Program storage may also be organized into useful data structures such as a stack or heap. The peripherals and interface and the general purpose I/O interface may interface to external input or output devices. Examples of external input or output devices include any electronic device capable of sending or receiving an electronic signal such as keyboards, mice, printers, scanners, digital sensors, analog sensors, Ethernet, analog to digital converters, ADC, UART, USB, etc. Program storage, local memory, peripherals and interface, and general purpose I/O interface may be contained on the circuit board of the CPU. The microprocessor 210 may further include a screen whereby the graphics adapter 616 may alter the display, such as at validation or denial of a ticket. In some embodiments, any of these parts may be external to the CPU.

The microprocessor 210 may include a symmetric multiprocessor (SMP) system or other configuration including a plurality of processors 302 connected to system bus 304. In some embodiments, a single processor 302 may be employed. A memory controller/cache 306 may be connected to the system bus 304, which may provide an interface to the local memory 308. An I/O bridge 310 may be connected to the system bus 304 and may provide an interface to an I/O bus 314. The I/O bus 312 may be utilized to support one or more buses and corresponding devices, such as bus bridges, input-output devices (I/O devices), storage, network adapters, etc. Thus, a network adapter may be coupled to the system to enable the data processing system to become coupled to other data processing systems or remote printers or storage devices through intervening private or public networks.

In some embodiments, devices such as a graphics adapter 316, storage 318 and a computer-usable storage medium 320 may be connected to the I/O bus 312 and may have computer usable program code embodied thereon. The computer-usable program code may be executed, e.g., by one or more processors to implement one or more aspects of the present disclosure, for example, to implement any aspect of any of the methods, processes and/or system components with respect to the present disclosure. For instance, the computer usable program code can be utilized to implement a linker that implements any one or more of the methods described herein. Moreover, the computer-usable program code may be implemented in the local memory 308 or other suitable storage media.

In some embodiments, the reporting components 116 may include an attachable and/or detachable self-contained unit. In these embodiments, the reporting components 116 may include a case that is shaped to snap-fit over the piston receiving end of the injection device 100. Furthermore, sensors, such as the temperature sensor 202, may detect the ambient temperature of the reporting components 116 as an approximation of temperature of the pharmaceutical in the barrel 102.

Figure 4:
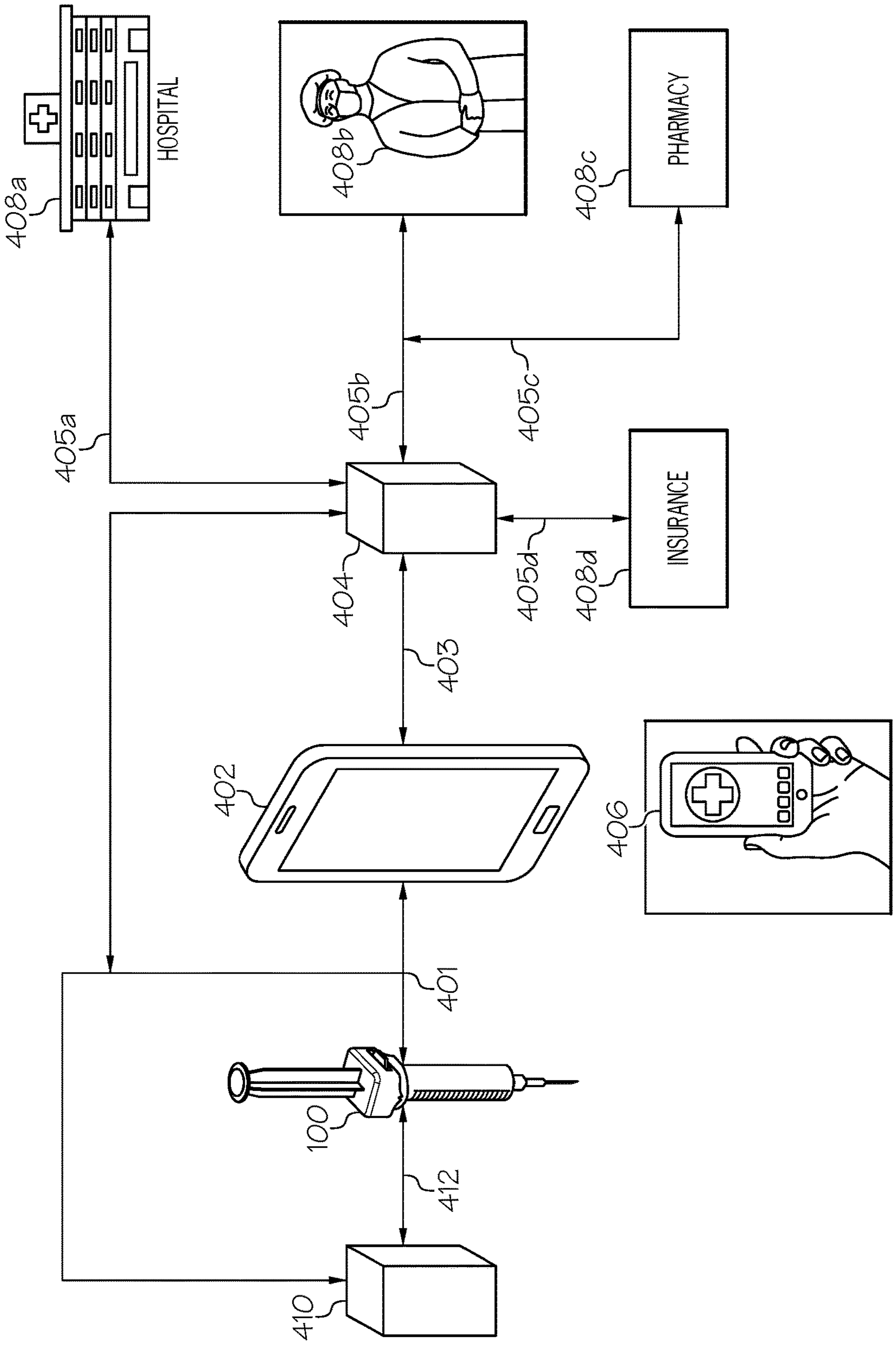
FIG. 4 is a diagram that illustrates data generation by the injection device and data sharing according to some embodiments of the present disclosure.

FIG. 4 illustrates a diagram of data generation by the injection device 100 and data sharing. A processor and/or microprocessor of a patient device 402 and/or a server 404 may be substantially similar to the microprocessor 210 such that the patient device 402 and/or the server 404 may be programmable to carry out the processes.

Internet connection, such as a wireless connection 401 and/or internet connection 403, 405*a-d* may be established via internet connection hardware such as a circuit configured as a wired or wireless internet adapter or other means of electronic communication. In some embodiments, the wireless connection 401 may connect the injection device 100 to the patient device 402 over the wireless interface 204. For example, the internet connection 403, 405*a*-405*d* may be substantially similar to the wireless connection 401. In some embodiments, the internet connection 403, 405*a*-405*d* may include an Ethernet jack for wired connection directly or indirectly to a local router, modem, server, transmitter tower such as a radio tower, satellite and/or any other gateway to the worldwide web. In some embodiments, the internet connection 403, 405*a*-405*d* may include a wireless card or circuit. The wireless card may be wirelessly connected directly or indirectly to a local router, modem, server, transmitter tower such as a radio tower, satellite and/or any other gateway to the worldwide web. In some embodiments, the internet connection 403, 405*a*-405*d* may be wirelessly connected directly to another computer or handheld device, such as a phone, watch, or tablet. In other embodiments, the internet connection 403, 405*a*-405*d* may engage in electronic communication with another computer or device by infrared (IR) transmitter and receiver, Bluetooth connection, fiber optic connection, cellular or mobile network (e.g., fixed area transceivers), or any other connector for transferring electronic data. For example, the internet connection 403, 405*a*-405*d* may send data over Bluetooth connection to a computer, server, or other devices. The server 404 may then upload the data for access via the internet connection 403, 405*a*-405*d*. Additional embodiments include an internet connection 403, 405*a*-405*d* that is configured to send the store data over Bluetooth, infrared communication, etc. directly to the server 404. Internet connection 403, 405*a*-405*d* may transmit data via analog or digital signal, UDP or TCP, http, https, ssh, ftp, sftp, etc., or any other means to transfer electronic data.

The internet connection 403 may provide for electronic communication between the patient device 402 and the server 404. The internet connection 405*b* may provide for electronic communication between the server 404 and a health care stakeholder, such as a physician 408*b*. Internet connection 405*c* may provide for electronic communication between the server 404 and a health care stakeholder, such as a pharmacy 408*c*. The internet connection 405*d* may provide for electronic communication between server 404 and a health care stakeholder, such as an insurance provider 405*d*.

In some embodiments, the patient device 402 may include an app 406, such as by having the app 406 installed thereon. The app 406 may manage the wireless connection 401 and electronic communications between the injection device 100 and the patient device 402. For example, the app 406 may be registered to a patient, such that the patient may be verified. Patient verification may be provided through a password protected login system and/or a digital certificate system. Once verified, the patient may review treatment data stored by the server 404 by communication between the patient device 402 and the server 404 over internet connection 403. Treatment data may include treatment history and may include patient compliance data.

In some embodiments, verification of the patient may unlock the locking mechanism 212 in the injection device 100 such that pharmaceutical may be administered via the injection device 100. In some embodiments, the injection device 100 may be preregistered to a patient, such as by a pharmacy 408*c* that fills the prescription for the drug in the injection device 100. The app 406 may provide patient verification data to the microprocessor 210. The microprocessor 210 may unlock the locking mechanism 212 upon patient verification. In some embodiments, the injection device 100 may not necessarily be preregistered to a patient. In these embodiments, the app 406 may provide patient information, such as a patient ID, or the app 406 may record injection device information, such as an injection device ID. The app 406 may signal that injection may proceed, and the microprocessor 210 may unlock the locking mechanism 212.

In some embodiments, the wireless connection 401 may establish electronic communication between the injection device 100 and the patient device 402. The injection device 100 may send the administration data 500 to the patient device 402 over the wireless connection 401. The wireless connection 401 may establish electronic communication between the injection device 100 and the server 404. The injection device 100 may send the administration data 500 to the server 404 over the wireless connection 401.

In some embodiments, one or more health care stakeholders 408*a*-408*d* may access the server 404 to review treatment data stored on the server 404 for corresponding patients. In this manner, stakeholders 408*a*-408*d* may make treatment and/or coverage decisions. For example, a provider (e.g., a hospital 408*a* or a physician 408*b*) may guide a noncompliant patient towards compliance in order to achieve better treatment outcomes. Additionally, if the desired treatment outcome is not achieved by compliance, alternative treatments may be chosen. Insurance provider(s) 408*d* may incentivize compliance through allowable avenues or vehicles, such as with additional coverage and/or lower premiums. However, insurance provider 408*d* may intervene when non-compliance occurs, such as by withdrawing coverage for treatments wherein the patient is noncompliant. One or more pharmacy stakeholders 408*c* may compare treatment data to prescriptions in order to provide for timely refills available to encourage patient compliance and also to assess for compliance with a treatment regimen. This process may encourage compliance with the proper administration of prescribed pharmaceuticals.

Figure 5:
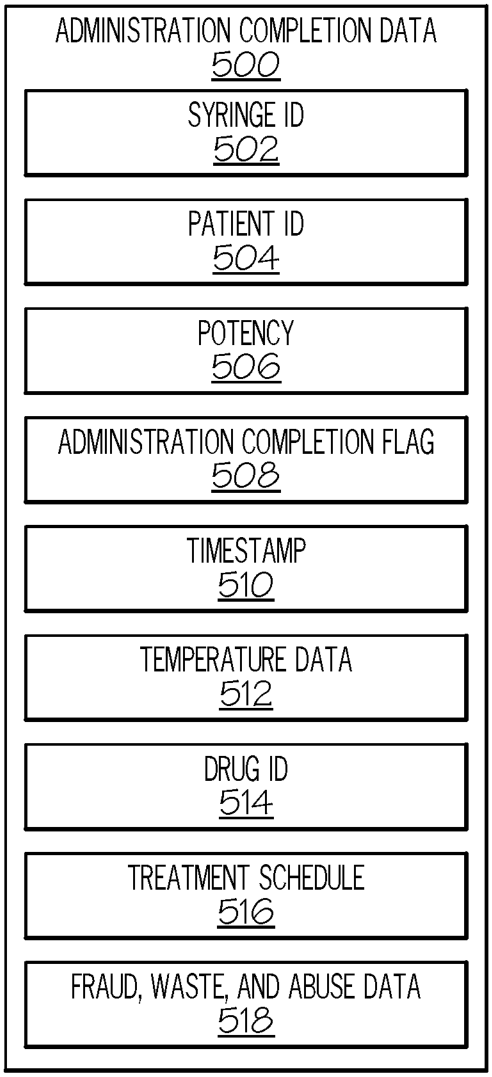
FIG. 5 is a block-level diagram that illustrates administration data as it can be stored on the injection device according to some embodiments of the present disclosure.

FIG. 5 illustrates a block-level diagram of the administration data 500 as can be stored on the injection device 100. The administration data 500 may include an injection device ID 502. In some embodiments, the injection device ID 502 can be associated with a manufacturing lot of the injection device 100 or of a pharmaceutical contained in the injection device 100. Furthermore, the administration data 500 may include a drug ID 514 of the contained pharmaceutical for identifying the drug and/or the manufacturing lot of the drug.

The administration data 500 may further include a patient ID 504. The patient ID 504 may be set by the pharmacy 408*c* or by the app 406. A potency 506 may include the volume and/or concentration of the entire amount of the injectable drug contained in the injection device 100. The administration data 500 may include an administration completion flag 508, such as a binary indication of whether the injection was completely administered, as detected by the injection device

100. Upon completion of injection administration, the administration completion flag 508 may be changed from False to True. Furthermore, upon completion of injection administration, the administration data 500 may be sent to the patient device 402 and/or the server 404. In some embodiments, the administration data 500 may include a treatment schedule 516. When an injection is missed, the injection device 100 may send the administration data 500 to the patient device 402 and/or the server 404 reflecting a missed injection (e.g., the administration completion flag 508 set to False). In some embodiments, the injection device 100 is configured to send the administration data 500 to the patient device 402 and/or the server 404 indicating an incomplete administration when the administration is started, but not completed. For example, if a load sensor indicated that an injection was not performed, or if a partial administration was injected.

The administration data 500 may include a timestamp 510. The server 404 may use the timestamp 510 to determine the compliance of the injection. The administration data 500 may further include temperature data 512 as detected by the injection device 100. The temperature data 512 may aid in the estimation of degradation of the pharmaceutical below the prescribed potency in the injectable.

In some embodiments, the administration data 500 may include a fraud, waste, and abuse data 518. The fraud, waste, and abuse data 518 may include an analog and/or digital force measurement as detected by a load sensor (described with respect to FIGS. 9A-9C). The server 404 may then determine whether an auto-injection was dispensed into the air (as a fraud, waste, and abuse rather than treatment). In alternative embodiments, the fraud, waste, and abuse data 518 may include a flag corresponding to whether the injection was legitimate or wasteful/fraudulent. In these embodiments, the microprocessor 210 may use the load sensor data to determine the flag. In these embodiments, the load sensor measurements may be compared to a predetermined force threshold, as injections into a patient may cause more resistance and corresponding higher force compared to a wasteful/fraudulent injection to the air. In some embodiments, a change in force (e.g., a delta) may be sensed and/or used to determine the legitimacy of the injection. For example, an intradermal, intravenous, subcutaneous, or intramuscular injection may be detectable by corresponding predetermined force thresholds (ordered by a pre-determined lowest force to highest force threshold).

In some embodiments, after transmission from the injection device 100, the administration data 500 may be used to make one or more of an insurance coverage determination, a medical treatment determination, and a manufacturing determination. The insurance coverage determination may involve receiving of the administration data 500 by an insurance company and making insurance coverage decisions based thereon, such as increasing or lowering insurance rates or claim payouts based upon whether data indicative of a legitimate injection or a fraudulent injection is included in the administration data 500. The medical treatment determination may involve receiving of the administration data 500 by a medical facility and/or one or more medical practitioners. The one or more medical practitioners may make adjustments to the treatment of a patient based on the administration data 500. The manufacturing determination may involve receiving of the administration data 500 by one or more manufacturers, such as a manufacturer of the injection device 100. The one or more manufacturers may make design adjustments, assembly adjustments, factory adjustments, or any other suitable manufacturing determinations based on the administration data 500.

In some embodiments, the injection device 100 may be paired to a modem 410. The modem 410 may be substantially similar to wireless module 204. For example, the modem 410 may be in electronic communication with the patient device 402, server 404, or the internet. The electronic communication connection may occur via ethernet, wireless, Bluetooth, cellular connection, etc. In this manner, the injection device 100 may not necessarily be connected directly to the server 404 or to cellular towers. The injection device 100 may pair to the modem 410 via a modem connection 412. The modem connection 412 may be substantially similar to wireless connection 401. For example, the modem connection 412 may allow electronic communication between the injection device 100 and the modem 410. The modem connection 412 may be wireless or wired, and may be Bluetooth, Bluetooth low energy, cellular, or use any other suitable protocol or means of data transmission. In some embodiments, identifying information, such as the injection device ID 502, the patient ID 504, the potency 506, the drug ID 514, etc., stored on the injection device 100 may be set by the manufacturer, pharmacist, or other providers before receipt by the patient. In some embodiments, the injection device 100 may be set with a modem ID corresponding to the modem 410 of a particular patient for verification of the modem 410 of the patient with the injection device 100 and pharmaceutical contained therein. In some embodiments, a pharmacist or other provider of the injection device 100 may update the patient's modem 410 with identifying information, such as the injection device ID 502, the patient ID 504, the potency 506, the drug ID 514, the temperature data 512, the treatment schedule 516, and/or fraud, waste, and abuse data 518. The identifying information of the injection device 100 may be compared to identifying information on the modem 410. If the identifying information matches, e.g., the patient ID 504 and the drug ID 514 match between the injection device 100 and the modem 410, then the injection device 100 may establish electronic communication with the modem 410 to send the administration data 500 to the server 404 through the modem 410. In this manner, the modem 410 may include a cellular module and the injection device 100 and subsequent reporting injection devices may connect to the modem 410 to send the administration data 500 to the modem 410, which may send the administration data 500 over the cellular connection. In some embodiments, establishing a connection with the modem 410 may also unlock the injection device 100 to allow injection.

Figure 6:
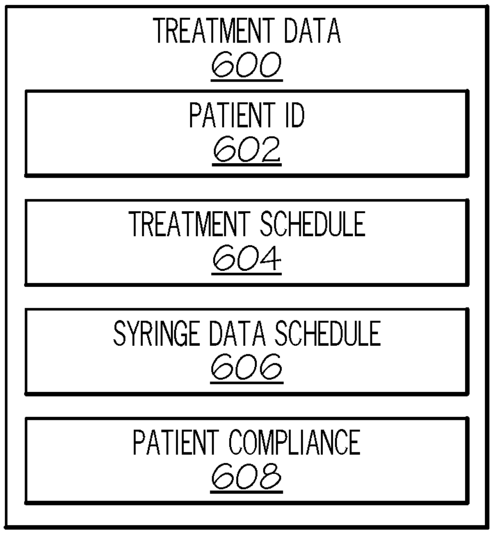
FIG. 6 is a block-level diagram that illustrates treatment data as it can be stored on a server according to some embodiments of the present disclosure.

FIG. 6 illustrates a block-level diagram of treatment data as can be stored on the server 404. The treatment data 600 may be stored, collected, and/or calculated by the server 404. For example, treatment data 600 may correspond to a patient associated with a patient ID 602. A corresponding treatment schedule 604, as prescribed by physician 408*b* may be stored. The treatment schedule 604 may include prescribed potencies and prescribed injection timings. For example, the treatment schedule 604 may include the prescribed pharmaceuticals, corresponding potencies, and prescribed injection regularity (e.g., daily, twice daily, etc.).

In some embodiments, an injection device data schedule 606 may be stored and/or modified by the server 404. The injection device data schedule 606 may include the injection device data history received by the server 404, which corresponds to the patient. For example, the injection device data schedule 606 may include the temperature of the pharmaceutical, the timestamp of administration, the potency, the administration completion flag, the injection device ID, the patient ID, the drug ID, etc.

In some embodiments, patient compliance 608 may be stored and/or calculated by the server 404. The patient compliance 608 may be determined by comparing the treatment schedule 604 to the injection device data schedule 606. If the injection device data schedule 606 is substantially similar with regard to the drug ID, the potency, and the injection timing to the treatment schedule 604, then the patient compliance 608 may be set to reflect patient compliance. Otherwise, the patient compliance 608 may be set to reflect patient non-compliance. In some embodiments, the patient compliance 608 may be stored with regard to the full history of data recorded, by year, by month, by week, and/or by day.

Figure 7:
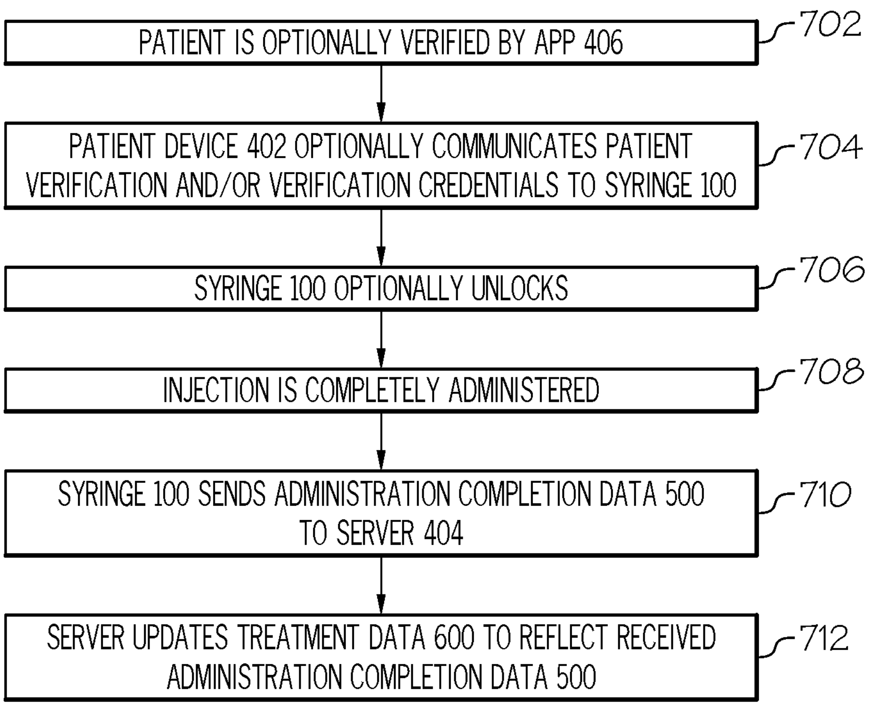
FIG. 7 is a block-level diagram that illustrates sending an administration data to the server according to some embodiments of the present disclosure.

FIG. 7 illustrates a block-level diagram of a method 700 of sending the administration data 500 to the server 404. In optional step 702, the patient may be verified by the app 406 on the patient device 402. In some embodiments, the patient device 402 may indicate that the patient is verified and/or may send the patient verification data over the wireless connection 401. The patient may be verified by username, password, patient ID, and/or digital certificate. In some embodiments, the patient may be verified by RSA key, fingerprint by the sensor of the patient device 402, and/or facial recognition by a camera of the patient device 402. In some embodiments, patient verification may include two-factor verification, wherein two methods may be required to satisfy patient verification. For example, the app 406 may include a code or key that corresponds to the patient, but the patient must also provide fingerprint and/or facial verification through the patient device 402.

In optional step 704, the patient device 402 may communicate patient verification and/or verification credentials to the injection device 100. Later, the injection device 100 may unlock the locking mechanism 212 based on positive patient verification. In some embodiments, the microprocessor 210 may perform verification based on one or more of username, password, patient ID, face verification, retinal verification, vocal verification, fingerprint verification, and/or digital certificate. However, embodiments include receiving an indication of positive patient verification as performed by the app 406, the patient device 402, and/or the server 404.

Upon verification, the injection device 100 may unlock the locking mechanism 212 such that the piston 106 may be compressed to administer the contained pharmaceutical.

In step 706, the injection device 100 may unlock, allowing for the administration of the drug in the barrel 102. However, in some embodiments, the injection device 100 may be prevented from unlocking according to the patient ID and/or the temperature data, such as when patient identification is not verified or when temperature data indicates that cold chain storage has been broken for the corresponding drug.

In some embodiments, the locking mechanism 212 may be reset from the locked position to the unlocked position in this step. For example, the microprocessor 210 may generate the administration data 500 that can correspond to the current injection upon unlocking the injection device 100. The administration completion flag 508 may be set to False upon beginning administration of the injection. In some embodiments, the administration completion flag 508 may not necessarily be changed until the head 112 is fully compressed to the barrel 102, such that partial injections may be reported. The microprocessor 210 may thus cause the administration data 500 to be sent to the server 404 after a predetermined elapsed time following unlocking the injection device 100 and/or load sensor detection, even if the switch 206 does not indicate that injection has occurred.

In step 708, the injection may be completely administered to the patient. In this step, the head 112 may be substantially fully compressed when the injection is substantially completely administered. The magnet 114 may be sufficiently proximate to the switch 206 such that the magnetic field may be detected, and an administration completion may be triggered. In some embodiments, a mechanical switch may be pressed to trigger notification of administration completion rather than or in addition to the magnet 114 being sufficiently proximate to the switch 206. In some embodiments, the administration data 500 may be generated upon detection of the magnetic field, wherein the administration completion flag 508 reflects the completed injection. For example, the administration completion flag 508 may be set to True. In some embodiments, administration completion may further trigger step 710, wherein the injection device 100 may send the administration data 500 to the server 404. In step 712, the server 404 may update the treatment data 600 to reflect the received administration data 500.

In some embodiments, the method 700 may be performed with respect to an attachable reporting module.

Figure 8:
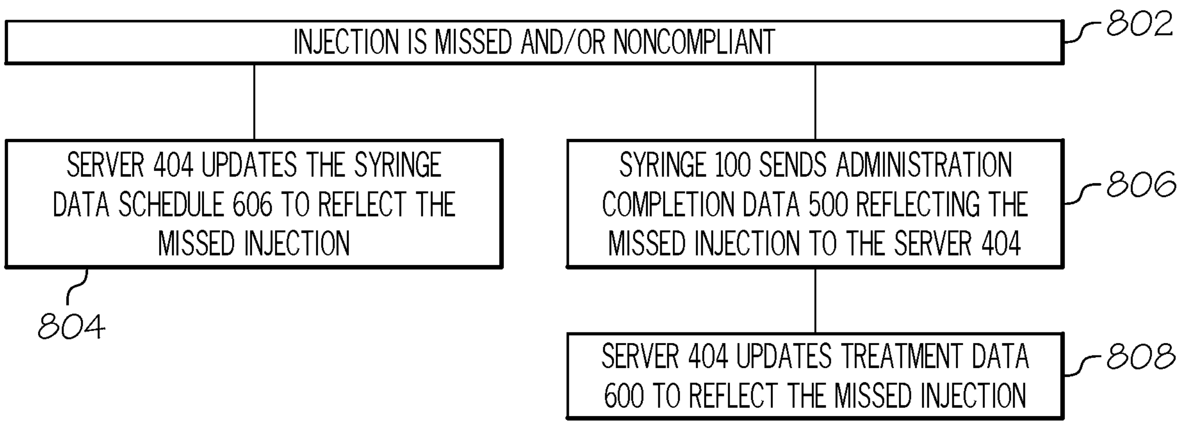
FIG. 8 is a block-level diagram that illustrates recording a missed injection according to some embodiments of the present disclosure.

FIG. 8 illustrates a block-level diagram of a method 800 of recording a missed injection. In step 802, an injection may be determined to be missed based on the treatment schedule 516 and/or 604. In some embodiments, the treatment schedule 604 may be stored on the server 404, and the server 404 may automatically update the treatment data 600 to reflect the missed injection 804. In other embodiments, the treatment schedule 516 may be stored on the injection device 100, and the injection device may send the administration data 500 reflecting the missed injection to the server 404 in step 806. Step 806 may further include sending the administration data 500 reflecting an incomplete injection (e.g., administration completion flag 508 set to False) to the server 404 when an injection is non-compliant. A noncompliant injection can include an injection where the administration was started, but not complete. Other non-compliant injections can include ejection of the drug from the injection device 100 without injecting into the patient, such as emptying the injection device 100 into the air. In step 808, the treatment data 600 may be updated to reflect the missed injection.

In some embodiments, the temperature sensor 202 may be used to record temperatures at a predetermined interval through the life cycle, such as transport, storage, etc., of the pharmaceutical. For example, the temperature sensor 202 could record temperatures daily, hourly, and/or every half-hour. In some instances, the temperature sensor 202 may record irregular temperatures, wherein the irregular temperature is known to risk degradation of the pharmaceutical. This temperature data 512 may be stored on the microprocessor 210 (e.g., the temperature data 512). Upon sending the administration data 500, the sent administration data 500 may include life cycle data, such as the temperature history (e.g., the temperature data 512).

In some embodiments, the temperature data 512 may be used to determine whether the pharmaceutical remains potent and/or safe for injection, and subsequently, whether providers, pharmacists, insurers, and other stakeholders should rely on, use, or pay for that pharmaceutical. The temperature data 512 may include a temperature compliance flag that may be positive when the pharmaceutical remains within a predetermined threshold of temperatures for that pharmaceutical (e.g., cold chain storage), as detected by the temperature sensor 202. The temperature data 512 may include a temperature compliance flag. For example, the temperature compliance flag may default to True and may be changed to False upon detection of a freezing of the pharmaceutical by the temperature sensor 202. The temperature compliance flag may be changed to False upon elevation of the temperature above the predetermined temperature range threshold and/or temperature drop below the predetermined temperature range threshold. In some embodiments, the temperature data 512 and or temperature compliance flag may allow for a time tolerance for exceeding the predetermined temperature range (except that freezing is not allowed in some embodiments). In embodiments containing Humira, Enbrel, or Remicade, the temperature compliance flag may remain True unless the temperature of the drug is detected outside the range of 2 to 8 degrees Celsius. In some embodiments, the temperature compliance flag may not necessarily be changed until extended storage at room temperature is detected. In the embodiments of Humira and Enbrel, the temperature compliance flag may become False when the injection device 100 containing the drug is stored at room temperature for over 14 days. In embodiments having Remicade, the temperature compliance flag may become False when the injection device 100 is stored at room temperature for over 24 hours.

In some embodiments, the predetermined temperature range thresholds may correspond to the particular pharmaceutical in the corresponding injection device 100. The predetermined temperature range thresholds may be set by a manufacturer, the pharmacist, an insurance provider, and/or a health care provider.

In some embodiments, the injection device 100 may include a temperature safety feature to prevent the injection of degraded pharmaceuticals. For example, the locking mechanisms 212 may remain locked after the temperature compliance flag of the temperature data 512 becomes False, regardless of verification of patient identification.

In some embodiments, the microprocessor 210 may be configured to calculate a degradation risk correlating to the pharmaceutical. In these embodiments, if the degradation risk is above a predetermined threshold, then the locking mechanism 212 may prevent injection, even if the other criteria, such as patient verification, are satisfied. In some embodiments, the microprocessor 210 may include a timing circuit configured to calculate the degradation risk. In some embodiments, the timing circuit may be used with the temperature sensor 202 to detect when the injection device 100 and/or pharmaceutical is removed from temperature-controlled storage. The timing circuit may be used to ensure that the injection is made before a predetermined elapsed time. In these instances, the locking mechanism 212 may prevent injection after the predetermined elapsed time from removal from storage, even if the other criteria are satisfied.

In some embodiments, the injection device 100 may be a multi-use system, such that the injection device may be reusable and/or the reporting components 116 may be reusable. In these embodiments, the needle 104 may be replaceable and the reporting components 116 and/or the administration data 500 may be reset upon changing the needle 104. Furthermore, the reporting components 116 and/or the administration data 500 may be reset upon snap-fit of the reporting components 116 to a new injection device 100. Resetting the reporting components 116 and/or the administration data 500 may be triggered by a mechanical switch, such as when the mechanical switch is closed or opened. Changing the needle 104 and/or snap fitting the reporting components 116 to the injection device 100 may trigger the mechanical switch. However, many biologics may be provided as prefilled injection devices 100 intended for single-use administration. In these embodiments, the needle 104 may not necessarily be changed.

In some embodiments, the method 800 may be performed with respect to an attachable reporting module.

Figure 9A:
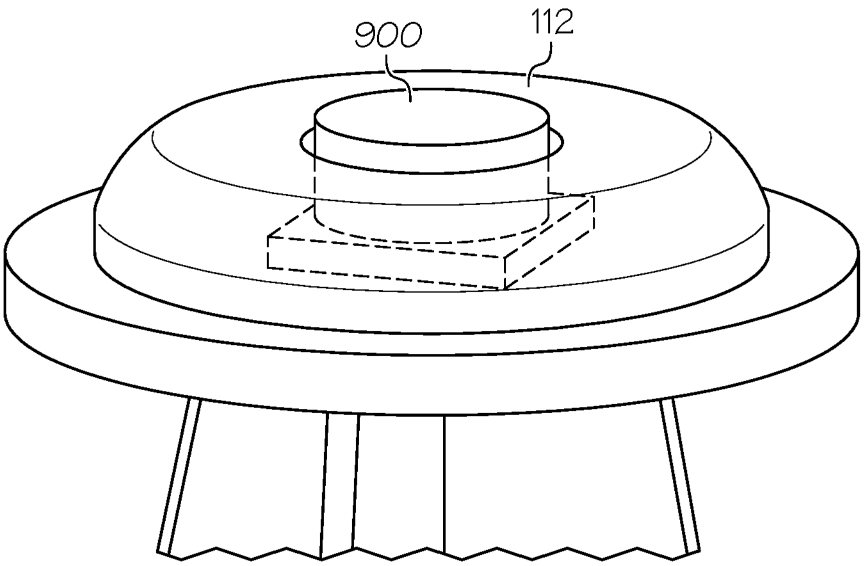
FIG. 9A is a diagram that illustrates a head of the reporting injection device comprising a load sensor according to some embodiments of the present disclosure.
Figure 9B:
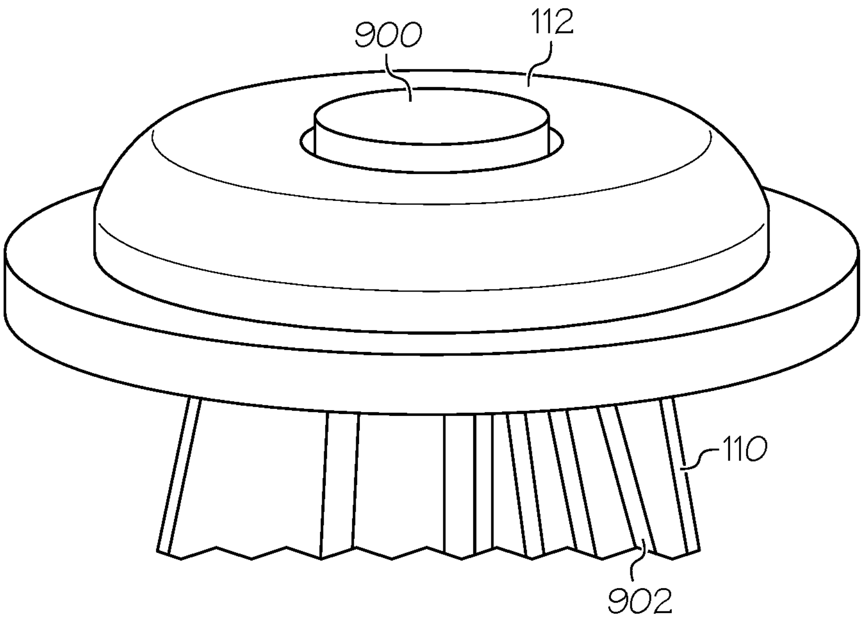
FIG. 9B is a diagram that illustrates a conductor of the reporting injection device according to some embodiments of the present disclosure.
Figure 9C:
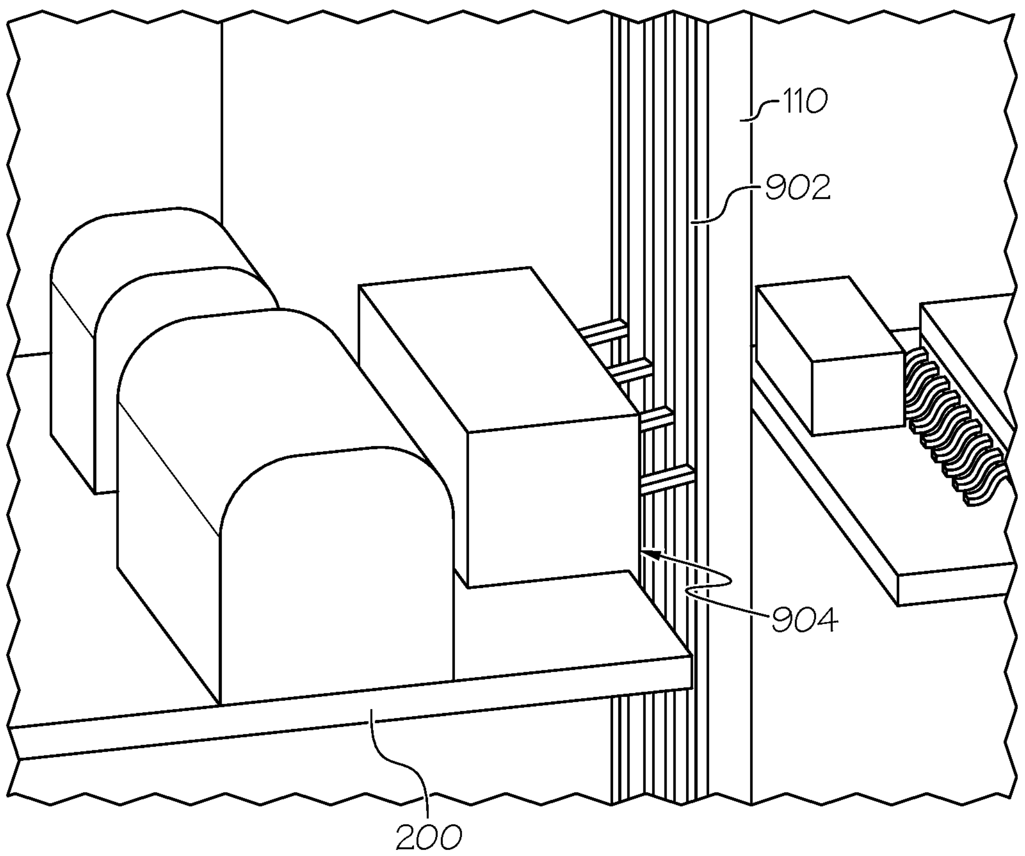
FIG. 9C is a diagram that illustrates the interaction of a stalk of the reporting injection device and a load sensor receiver according to some embodiments of the present disclosure.

FIGS. 9A-9C illustrate embodiments of the injection device 100 including a load sensor. The load sensor may be positioned on the needle proximate the barrel 102. In some embodiments, the load sensor may be positioned within the barrel 102 such that a pressure gradient in the injection device may be detected. The load sensor may be in electronic communication with the microprocessor 210 such that the load sensor may send detected pressure to the microprocessor 210. The microprocessor 210 may record and/or send the pressure data with the administration data 500. The load sensor may detect, for example, subcutaneous applied pressure, such as to determine that an intermuscular injection is occurring. In some embodiments, the locking mechanism 212 may lock in response to an absence of appropriate pressure detection by the load sensor, thereby preventing injection. In some embodiments, the injection may be allowed, by the locking mechanism 212 being unlocked, but administration data 500 may include a pressure data reflecting improper pressure detected. In some embodiments, the administration data 500 includes pressure data from the load sensor, regardless of whether appropriate pressure has been detected.

FIG. 9A illustrates embodiments of the injection device 100 wherein the head 112 of the injection device 100 comprises a load sensor 900. In some embodiments, the load sensor 900 may be present with the magnet 114. The load sensor 900 may include a force sensor. For example, some force sensors include a force-sensing resistor that includes a material that changes resistance when a force, pressure, or mechanical stress is applied. Such materials may include a conductive polymer. The changes in resistance may be interpolated to correspond to the force applied, such that the force applied to inject the drug from the barrel 102 can be measured. The measured force may be higher when injecting into a patient, such as an intermuscular injection, rather than dispensing the drug through the needle without injection. By way of example, the additional force may result from mechanical resistance of the body of the patient to the injection compared to the relatively lower resistance when dispensing the drug into the air.

In some embodiments, a predetermined force threshold may be used to determine whether dispensing the drug resulted in a compliant injection or a noncompliant fraud, waste, and abuse. For example, a measured force greater than the predetermined force threshold may correspond to a compliant administration of the drug. Furthermore, measured force less than the predetermined threshold may correspond to a wasteful or fraudulent occurrence, such as dispensing the drug into a sink.

Example force sensors may include the Honeywell FSA series, FSG series, FSS series, TBF series, or 1865 series. For example, the load sensor 900 may be able to measure from about 1 bar to about 10 bar, about 100 kPa to about 1 MPa, or about 15 psi to about 150 psi in pressure. The load sensor 900 may include millivolt analog output. Alternative embodiments may include other load cells that may be electronically read by the microprocessor.

FIG. 9B illustrates embodiments of the injection device 100 including a conductor 902. The load sensor 900 may be in electrical and/or electronic communication with the conductor 902. The conductor 902 may include one or more electrically conductive traces and/or wires that run the length of the stalk 110 such that the conductor 902 may remain in electrical communication with the circuit board 200 during the injection. In some embodiments, the conductor 902 may allow the load sensor 900 to be in electrical communication with the circuit board 200 and/or the microprocessor 210 before, during, and/or after the injection. In some embodiments, the load sensor 900 provides an analog output, the output can be relayed to the microprocessor for comparison to the predetermined force threshold or converted to digital measurement and comparison to the predetermined threshold.

FIG. 9C illustrates embodiments of the reporting injection device 100 wherein the stalk 110 includes a load sensor receiver 904. In some embodiments, the load sensor receiver 904 may be in electrical communication with the conductor 902 and/or the circuit board 200. In this manner, the load sensor receiver 904 may relay electrical and/or electronic signals and/or information from the conductor 902 to the microprocessor 210. In some embodiments, the load sensor receiver 904 may convert analog signals to digital signals. In some embodiments, the load sensor that may convert the analog signal to digital, and the load sensor receiver 904 may relay the digital signal to the microprocessor 210. In some embodiments, the load sensor receiver 904 may relay the analog signal to the microprocessor 210 for conversion by the microprocessor 210, in embodiments wherein conversion is performed before comparison to the predetermined force threshold.

In some embodiments, the injection device 100 may include an automatic injection system in communication with the microprocessor 210. The automatic injection system may facilitate the automatic injection of one or more doses of a pharmaceutical from the injection device 100. The automatic injection system may facilitate automatic injection of the one or more doses at one or more of a specific injection rate, at a specified injection depth, and at a predetermined injectable temperature, the rate, depth, and temperature being measured by one or more of the sensors of the injection device 100, including the temperature sensor 202 and/or the load sensor. In some embodiments, the automatic injection system may be configured to facilitate the delivery of the dose by the injection device 100 according to an injection program among a library of injection programs stored in the microprocessor 210 or associated memory. In some embodiments, the automatic injection system may include a withdrawal mechanism, the withdrawal mechanism being configured to facilitate automatic withdrawal of the needle 104 from an injection site. In some embodiments, the automatic injection system may facilitate the delivery of the dose based on a prescribed profile for the recipient of the dose.

Figure 10A:
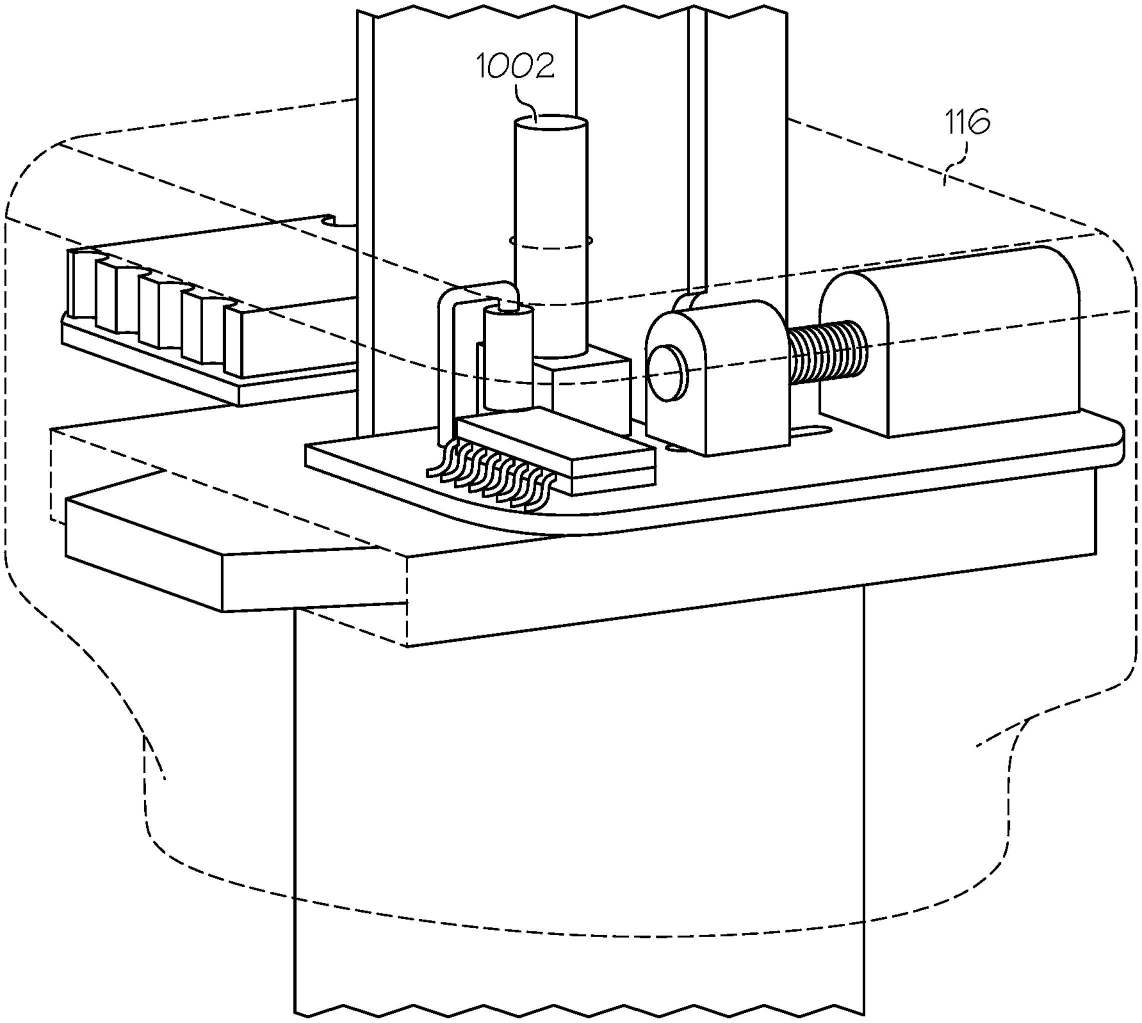
FIG. 10A is a diagram that illustrates a mechanical switch of the injection device according to some embodiments of the present disclosure.

FIG. 10A illustrates embodiments of the injection device 100 including a mechanical switch 1002. In some embodiments, the mechanical switch 1002 may replace the switch 206. The mechanical switch 1002 may be in electrical communication with the reporting components 116 such that the administration data 500 may be sent upon pressing the mechanical switch 1002. The mechanical switch 1002 may include a resistance spring. The mechanical switch 1002 may further include a circuit. Upon pressing the mechanical switch 1002, the circuit may become opened or closed. The change in the state of the circuit of the mechanical switch 1002 may trigger alteration and/or sending of the administration data 500.

Figure 10B:
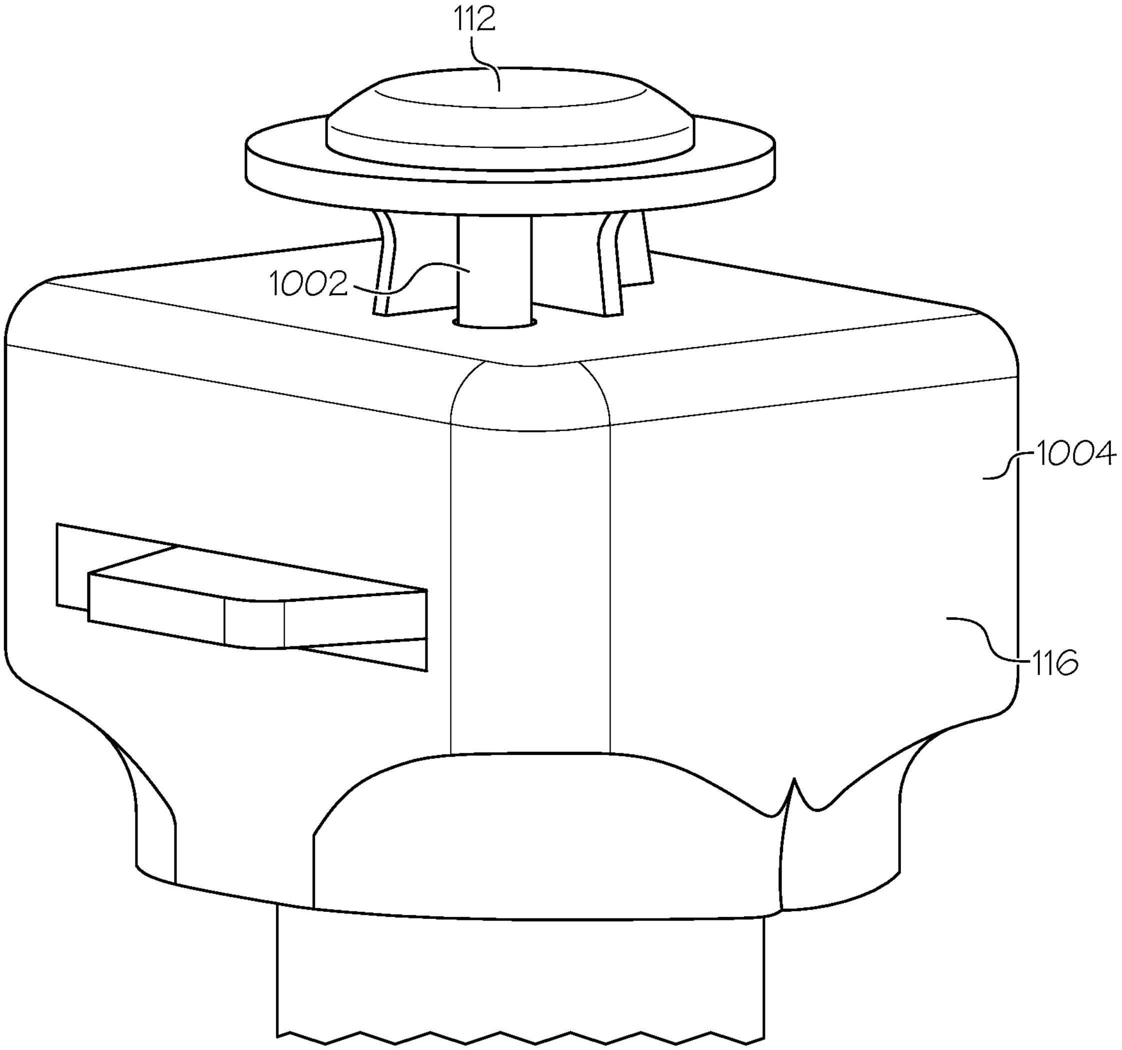
FIG. 10B is a diagram that illustrates an alternative view of the mechanical switch according to some embodiments of the present disclosure.

FIG. 10B illustrates embodiments of the injection device 100 including the mechanical switch 1002. The mechanical switch 1002 may extend beyond a housing 1004 of the reporting components 116. In some embodiments, the head 112 may not include the magnet 114. Rather, the head 112 may press the mechanical switch 1002 upon injection completion (e.g., when the head 112 is pressed to the housing 1004).

Figure 10C:
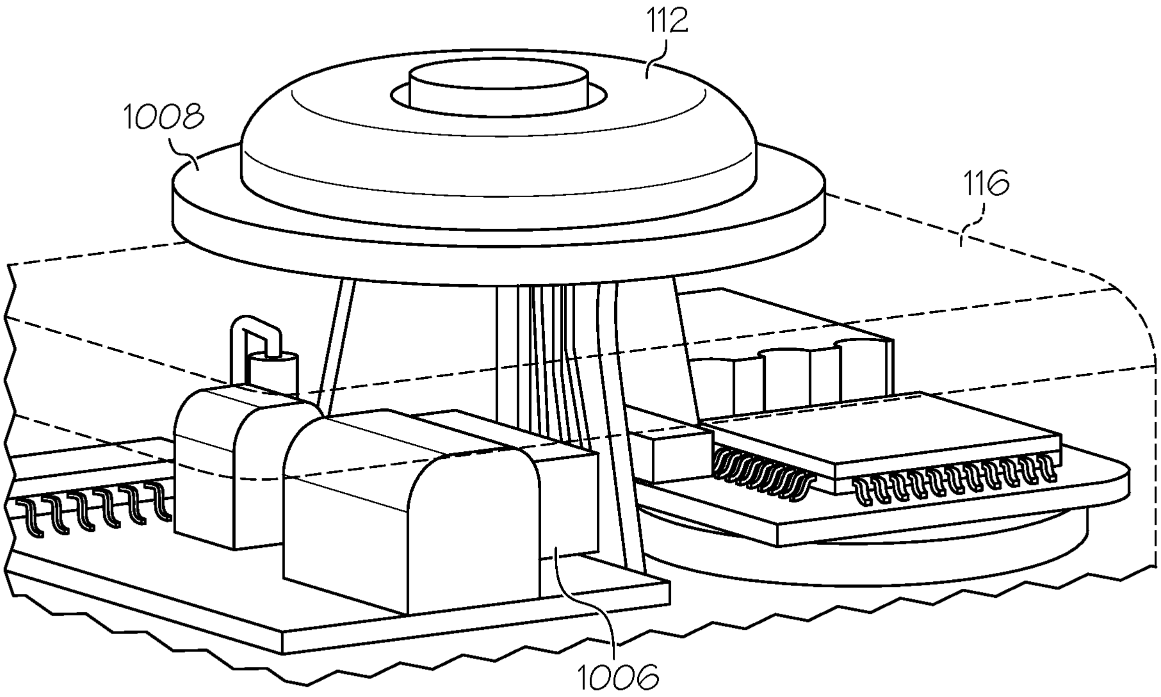
FIG. 10C is a diagram that illustrates another alternative view of the mechanical switch according to some embodiments of the present disclosure.

FIG. 10C illustrates embodiments of the injection device 100 including the mechanical switch 1002. The head 112 may include a stamping 1008 that may press the mechanical switch 1002 when fully pressed. The mechanical switch 1002 may include a mechanical switch contact 1006 that may be in electrical and/or electronic communication with the reporting components 116. Upon pressing the mechanical switch 1002, the reporting components 116 may generate or alter the administration data 500. Upon pressing the mechanical switch 1002, the reporting components 116 may send the administration data 500.

Figure 11A:
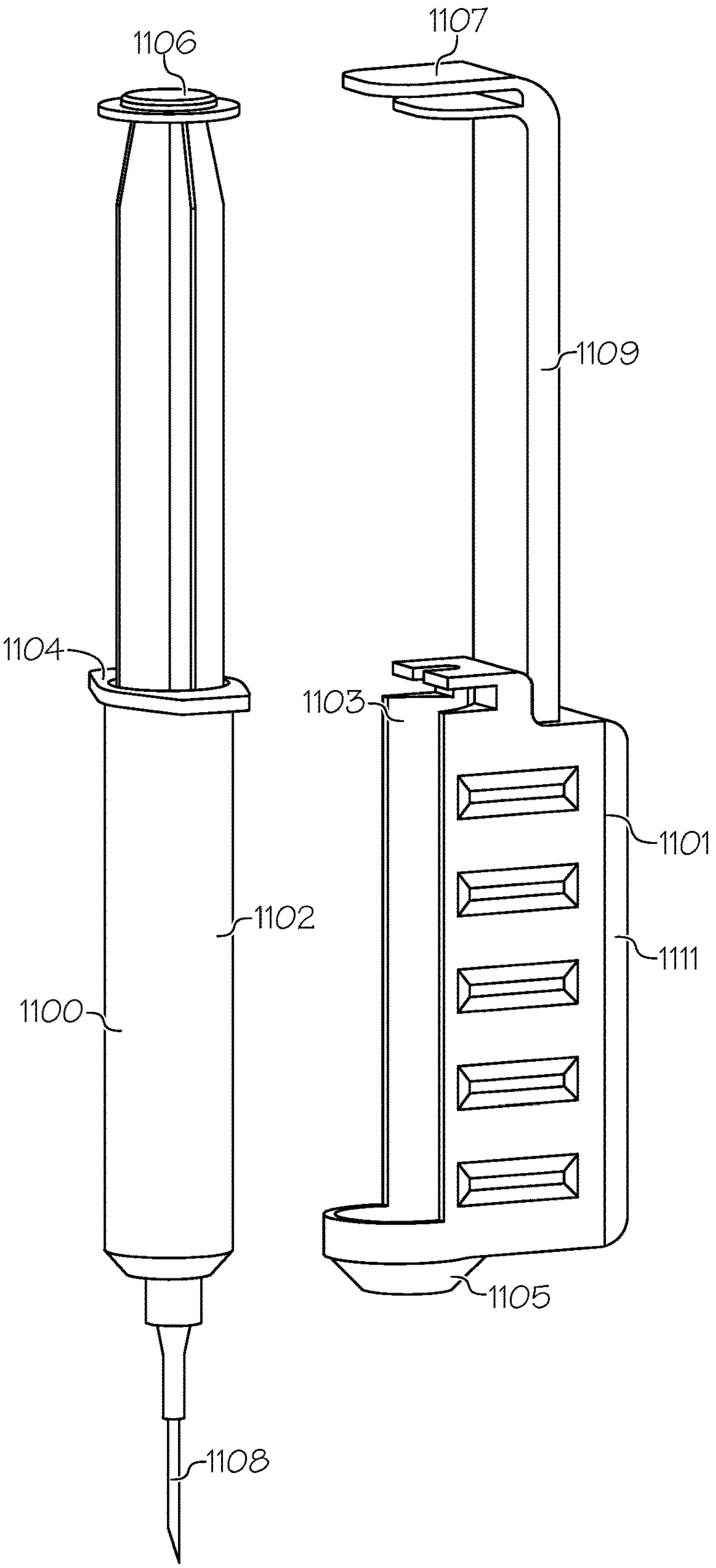
FIG. 11A is a diagram that illustrates an attachable reporting module according to some embodiments of the present disclosure.

FIG. 11A illustrates embodiments of the injection device 100 including an attachable reporting module 1101. The reporting module 1101 may be attachable and/or detachable from a standard injection device 1100. For example, the reporting module 1101 may include a barrel receiver 1105, a grip receiver 1103, and/or a head receiver 1107. The reporting module 1101 may further include a slide 1109 such that the head receiver 1107 may be pressed with a head 1106 of the standard injection device 1100. These structures may allow the reporting module 1101 to be attached to the standard injection device 1100 by frictional engagement. For example, a barrel 1102 of the standard injection device 1100 may be received in the barrel receiver 1105. The barrel receiver 1105 may include a conical or frusto-conical shape configured to receive and/or frictionally engaged the barrel 1102 proximate a needle 1108.

In some embodiments, the grip receiver 1103 may be configured to receive and/or frictionally engage a grip 1104 of the needle 1108. The grip receiver 1103 may be positioned the length of the barrel 1102 from the barrel receiver 1105. The grip 1104 may include flat flanges extending orthogonally from an end of the barrel 1102. The grip receiver 1103 may include a first support and a second support set apart at a sufficient distance to frictionally engage the flanges of the grip 1104 when inserted.

In some embodiments, the head receiver 1107 may be in slidable communication with a base 1111 of the reporting module 1101 via slide 1109 such that the head receiver 1107 may rest against and/or frictionally engage the head 1106 such that pressing the head receiver 1107 may press the head 1106 thereby administering an injection. The head receiver 1107 may include a single projection orthogonal to the slide 1109. Alternative embodiments include a first projection and a second projection. The first projection and second projection may be spaced apart such that the first projection may engage a distal side of the head 1106. The second projection may be distance sufficiently to engage a proximate side of the head 1106. In some embodiments, the second projection may frictionally fit against a feature, such as a stamping of the head 1106.

Figure 11B:
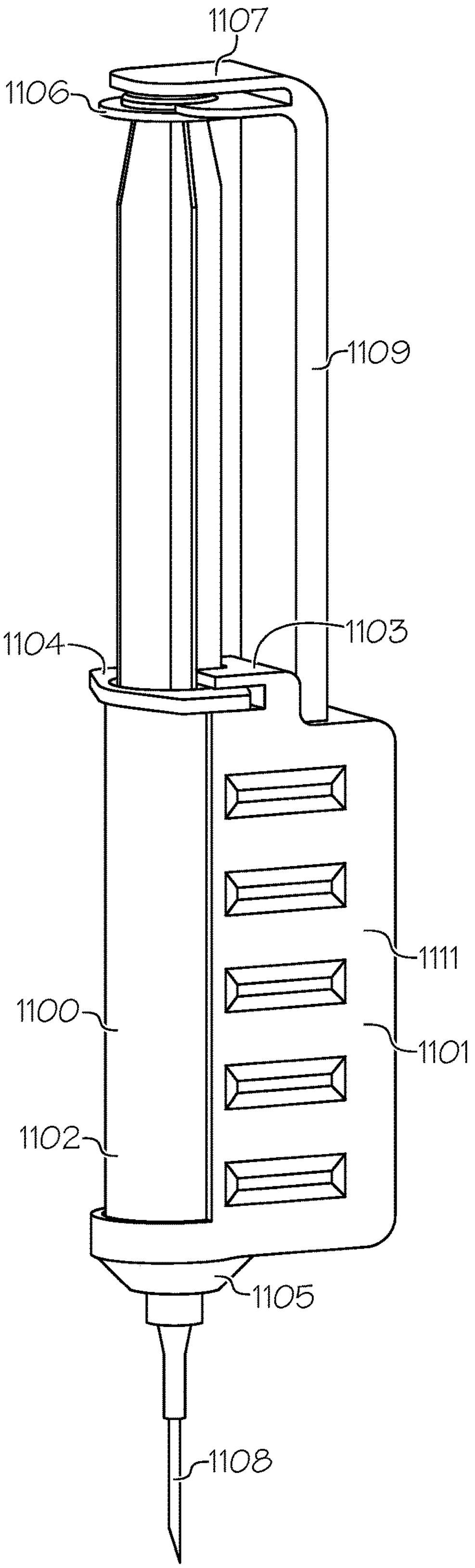
FIG. 11B is a diagram that illustrates the reporting module attached to a standard injection device according to some embodiments of the present disclosure.
Figure 11C:
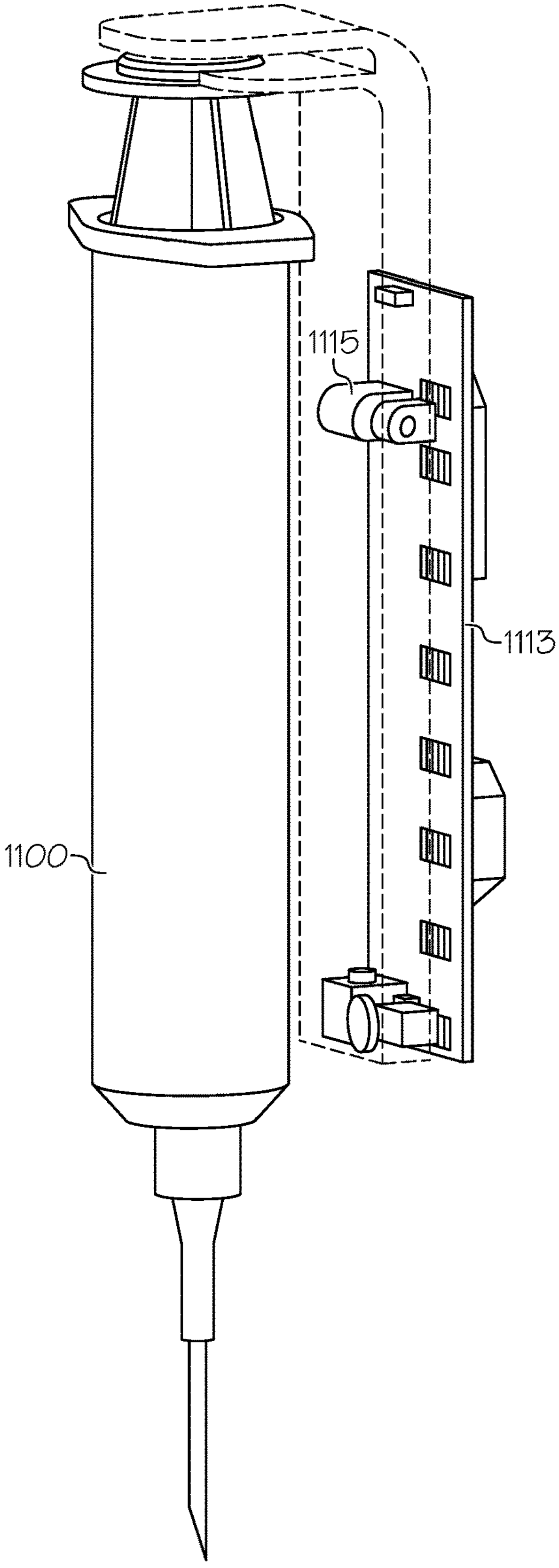
FIG. 11C is a diagram that illustrates the reporting components of the reporting module according to some embodiments of the present disclosure.

FIG. 11B illustrate embodiments wherein the reporting module 1101 is attached to a standard injection device 1100. The standard injection device 1100 may be frictionally engaged with the reporting module 1101. In some embodiments, the second projection of the head receiver 1107 may frictionally engage one or more features of a head 1106 of the standard injection device 1100, such as the stamping.

FIG. 11D-11G illustrate embodiments of the reporting components 1113 of the reporting module 1101. In some embodiments, the reporting components 1113 may be substantially similar to the reporting components 116. For example, the reporting components 1113 may include one or more of a temperature sensor, a wireless module, a switch, a battery, a microprocessor, a locking mechanism, etc. In some embodiments, the components may be in electrical and/or electronic communication with one another, such as via a circuit board. For example, locking mechanism 1115 may include a mortise formed in the slide 1109 that may receive a tenon of the locking mechanism 1115 to prevent injection when the reporting module 1101 is engaged to the standard injection device 1100.

Figure 11D:
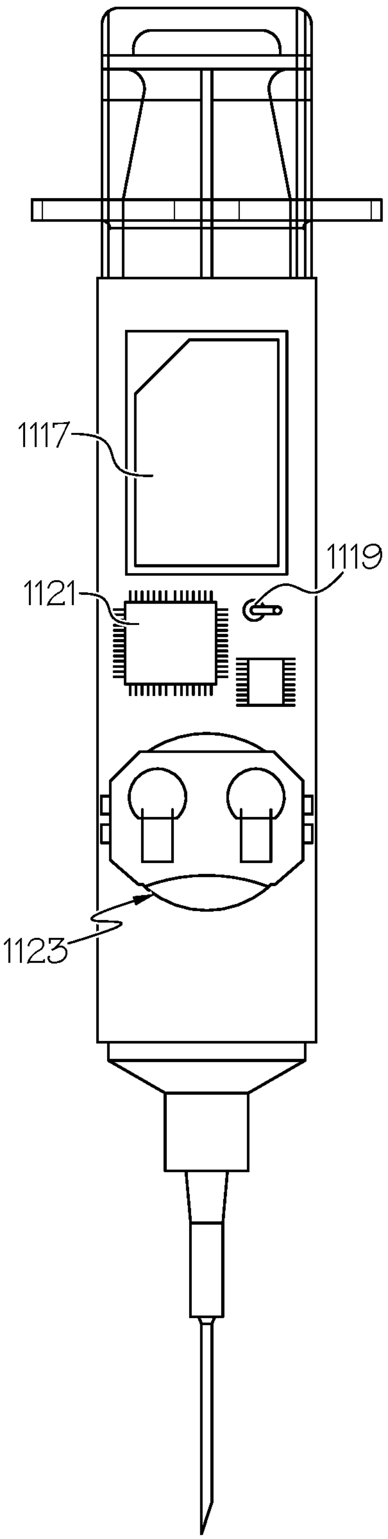
FIG. 11D is a diagram that illustrates an alternative view of the reporting components according to some embodiments of the present disclosure.
Figure 11E:
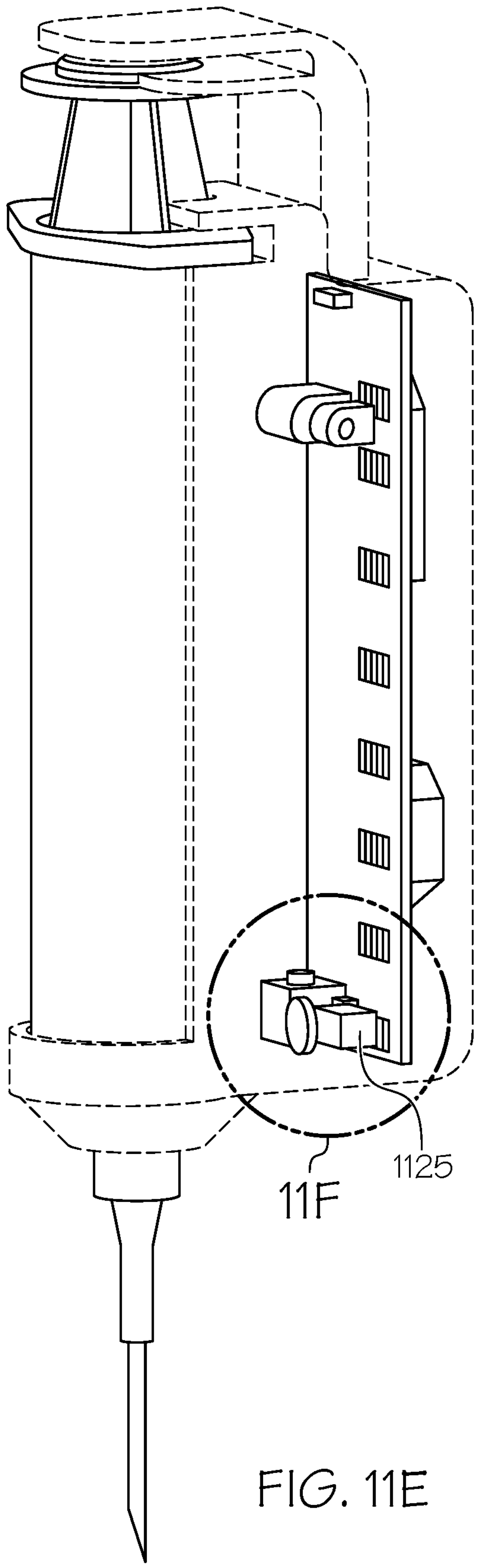
FIG. 11E is a diagram that illustrates an internal view of the reporting components according to some embodiments of the present disclosure.

With reference to FIG. 11D, in some embodiments, the reporting components 1113 may include a wireless module 1117, a temperature sensor 1119, a microprocessor 1121, and/or a battery 1123. The wireless module 1117, the temperature sensor 1119, the microprocessor 1121, and/or the battery 1123 may be substantially similar to the corresponding components of the reporting injection device 100. In some embodiments, the reporting components 1113 may include a switch 1125. The switch 1125 may include any structure sufficient for generating an electrical signal to the processor upon triggering the switch 1125. The switch 1125 may be a mechanical switch that is substantially similar to mechanical switch 1002. In other embodiments, the switch 1125 may be an electronic switch that is substantially similar to switch 206. In some embodiments, the switch 206 may be the mechanical switch 1002. In embodiments wherein the switch 1125 includes a Reed switch, the slide 1109 may include a magnet positioned to trigger the switch 1125 when fully pressed.

Figure 11F:
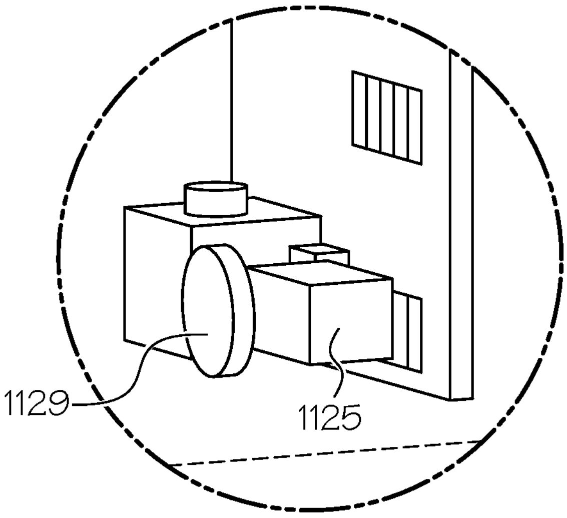
FIG. 11F is a diagram that illustrates a zoomed-in partial view of the reporting components according to some embodiments of the present disclosure.
Figure 11G:
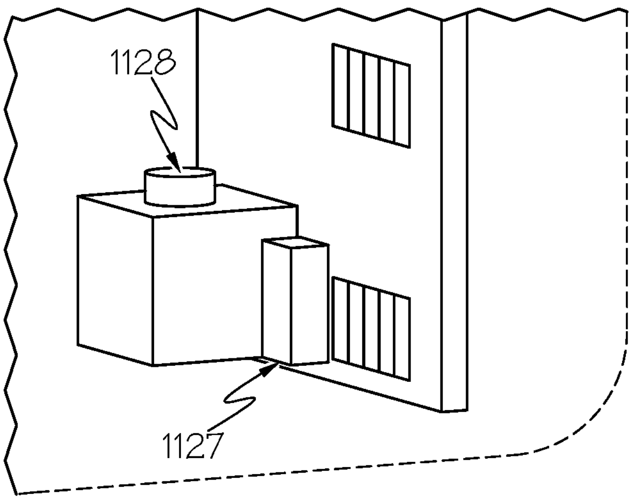
FIG. 11G is a diagram that illustrates an alternate zoomed-in partial view of the reporting components according to some embodiments of the present disclosure.

With reference to FIG. 11F, in some embodiments, the switch 1125 may include a Reed switch 1127 and a magnet 1129. The magnet 1129 may induce a magnetic field to trigger the Reed switch 1127 when the slide 1109 is compressed. The switch 1125 may include a microswitch 1128. The microswitch 1128 may include a miniature snap-action switch. The microswitch may include an electric switch that may be actuated by relatively low physical force, such as through the use of a tipping-point mechanism or an "over-center" mechanism.

Figure 11H:
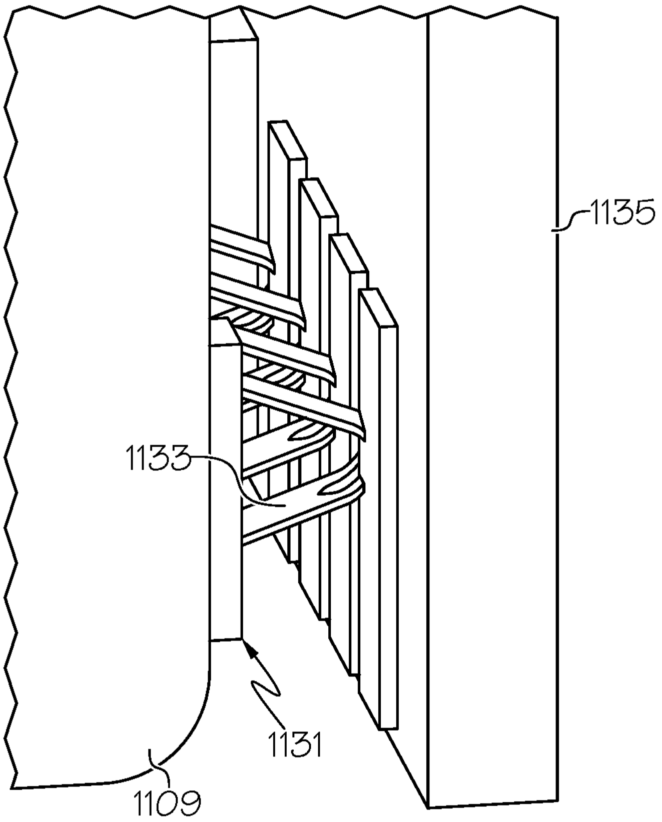
FIG. 11H is a diagram that illustrates a mechanical switch with a spring-loaded printed circuit board that may be pressed to open or close to trigger generation and/or sending administration data from the reporting components according to some embodiments of the present disclosure.

With reference to FIG. 11H, in some embodiments, the switch 1125 may include a mechanical switch 1131. The mechanical switch 1131 may include one or more spring-loaded PCB (printed circuit board) contacts. When the slide 1109 (also FIGS. 11A and 11B) is compressed, the spring-loaded PCB contacts 1133 may be pressed to open or close a circuit. The action of the spring-loaded PCB contacts may trigger generation and/or sending the administration data 500. A circuit board 1135 of the reporting components 1113 may include pressure-sensitive spring-loaded PCB contacts. In some embodiments, the circuit board 1135 may simply include contacts and the slide 1109 may include the spring-loaded contacts that provide electrical communication to trigger generating and/or sending the administration data 500 when the spring-loaded contacts are aligned with the circuit board contacts.

In some embodiments, the switch 1125, such as the spring-loaded PCB contacts, may reset the administration data 500. In this manner, the spring-loaded PCB or other mechanical switches may be pressed when attaching the reporting module 1101 to the standard injection device 1100 illustrated in FIGS. 11E and 11F.

Detailed embodiments of the present disclosure are disclosed herein; however, it is to be understood that the disclosed embodiments are merely exemplary of the disclosure, which may be embodied in various forms. Therefore, specific structural and functional details disclosed herein are not to be interpreted as limiting, but merely as a basis for the claims and as a representative basis for teaching one skilled in the art to variously employ the present disclosure in virtually any appropriately detailed structure.

Figure 12:
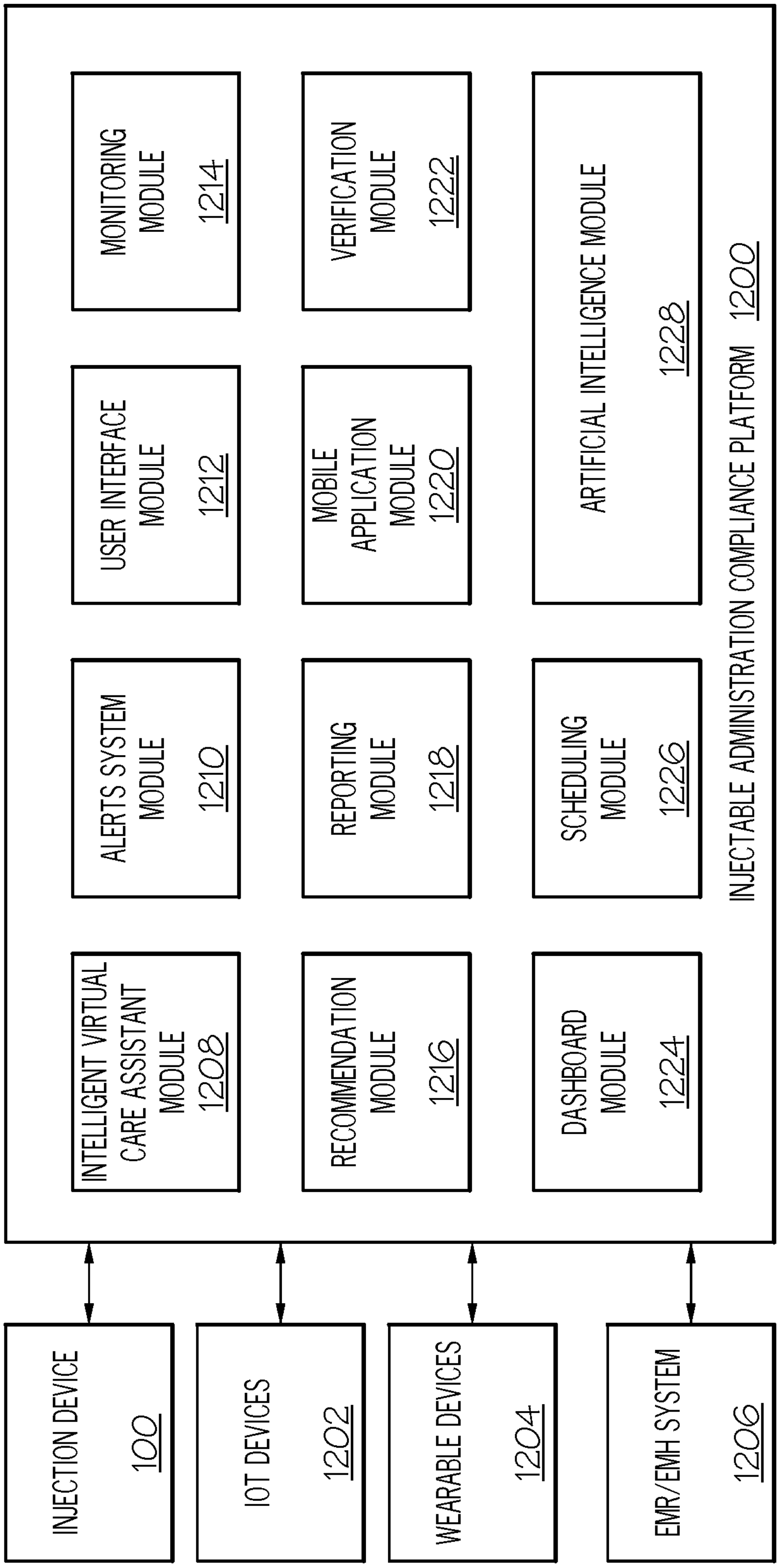
FIG. 12 is a block diagram that illustrates an injectable administration compliance management platform according to some embodiments of the present disclosure.

FIG. 12 illustrates embodiments of an injectable administration compliance management platform 1200. In some embodiments, the injection device 100 may be configured to transmit the administration data 500 to the injectable administration compliance management platform 1200. The management platform 1200 may be a software-based system and/or and Internet of Things (IoT)-based system and may be implemented in the server 404, may be cloud-based, may be a distributed system at least partially implemented in the microprocessor 210 of the injection device 100 and/or in a wearable device, or in any other suitable implementation. The management platform 1200 may be configured for real-time monitoring and management of adherence to an injectable administration plan. The management platform 1200 may receive data collected by one or more IoT devices 1202, one or more wearable devices 1204, one or more emergency medical record (EMR) and/or emergency health record (EHR) systems 1206. The one or more IoT devices may each include a camera, a wearable device, or a combination thereof. In some embodiments, the management platform 1200 may use one or more of the administration data 500, the IoT device data, the wearable device data, and data from the one or more EMR/EHR systems 1206 to make one or more of medical determinations, insurance coverage determinations, and manufacturing determinations. For example, one or more of the wearable devices 1204 and/or the IoT devices 1202 may record eating and/or sleeping data of a wearer of the one or more wearable devices 1204 and/or the IoT devices 1202 and transmit the recorded data to the management platform 1200. The management platform 1200 may automatically determine to change dosage, timing, or other attributes of injection by the wearer based on the recorded data and/or history thereof and transmit such determinations to the wearer.

In some embodiments, the management platform 1200 may be integrated with an EMR and/or EHR system 1206. Upon receipt of the administration data 500, the management platform 1200 may automatically populate one or more fields of the EMR and/or EHR system 1206 with some or all of the administration data 500.

In some embodiments, the management platform 1200 may include an intelligent virtual care assistant module 1208. The intelligent virtual care assistant module 1208 may be configured to perform tasks or services for a user or patient. In some embodiments, the tasks or services may be performed based on user commands. The tasks or services may be performed based on a plan specified by at least one of a physician, a physician's assistant (PA), a health care worker, and a caregiver. The intelligent virtual care assistant module 1208 may be configured to deliver alerts related to health, biometrics, medications, and/or injections, such as by delivering alerts via the wearable device 1204. For example, the intelligent virtual care assistant module 1208 may receive data indicative of an injection schedule according to which a patient should self-administer a drug via the injection device 100. At one or more times specified via the data indicative of the injection schedule, the intelligent virtual care assistant module may output an alert signal to the wearable device 1204. The wearable device 1204 can be configured to display an alert to the patient indicating that a self-injection via the injection device 100 is due according to the injection schedule. In some embodiments, the intelligent virtual care assistant module 1208 may be configured to provide a visual and/or an audible output, use an augmented reality system, use a virtual reality system, and/or be activated using a wake-word. For example, the intelligent virtual care assistant module 1208 may be configured to send a signal to a pair of smart glasses being worn by a patient, thereby causing the smart glasses to display an alert visible to a patient, display biometrics or other information to the patient such as via a chart, display an injection site to the patient, and/or display any other suitable two-dimensional or augmented reality information to the patient.

In some embodiments, the management platform 1200 may include an alerts module 1210. The alerts module 1210 may be configured to provide alerts to a patient and/or a user of the injection device 100. The alerts module 1210 may be configurable by the user and/or a health care provider. The alerts module 1210 may be automatically configured based on a prescribed injectable administration plan for the patient and/or user.

In some embodiments, the management platform 1200 may include a user interface module 1212 for controlling and/or configuring a user interface. The user interface module 1212 may be configurable by a patient, e.g., a user of the injection device 100. In some embodiments, the user interface module 1212 may be configured to automatically populate the user interface based on data from the injection device 100, such as the administration data 500 and/or a profile of the patient or other data collected from the patient, such as by the wearable. In some embodiments, the user interface module 1212 may be configured to receive data from the intelligent virtual care assistant module 1208 and configure and/or populate the user interface based on the data received. For example, the intelligent virtual care assistant module 1208 may send data indicative of a scheduled injection to the user interface module 1212, such as data indicating that an injection is due according to an injection schedule. In response to receiving the data, the user interface module 1212 may configure a user interface of the wearable device 1204 such that the user interface of the wearable device 1204 indicates to a patient that the injection is due.

In some embodiments, the management platform 1200 may include a monitoring and compliance module 1214 for monitoring user compliance. The monitoring and compliance module 1214 may distribute monitoring data to one or more of a set of health care providers, a set of health care payors, and a set of family members.

In some embodiments, the management platform 1200 includes a recommendation module 1216 for generating user recommendations. The recommendation module 1216 may generate recommendations based on one or more of a patient profile and a health care plan for a patient. The recommendation module 1216 may generate recommendations based at least in part on one or more similarities between a patient and a set of other patients.

In some embodiments, the management platform 1200 may include a reporting module 1218 for generating reports. The reporting module 1218 may automatically distribute reports to at least one of a patient, a health care worker, a manufacturer, and a health care payor. The reporting module 1218 may be configured based on at least one of a patient profile and a prescribed health care plan for the patient. In some embodiments, the reporting module 1218 may be configured to facilitate management of health care documentation by patients, health care workers, manufacturers, and/or payors, such as by facilitating electronic filling and/or signing of documentation, facilitating patient privacy, such as HIPAA compliance regarding healthcare documentation, allowing patients and family members to indicate opt-in or opt-out choices and/or other choices regarding treatment options, and managing and/or facilitating any other suitable aspect of health care documentation.

In some embodiments, the management platform 1200 may include a mobile application module 1220 for configuring, controlling, and/or transmitting data to and from a mobile application. The mobile application may be configured to communicate with the injection device 100 and/or the microprocessor 210. The mobile application may be configured based on at least one of a patient profile and a prescribed health care plan for the patient, i.e., the user of the mobile application.

In some embodiments, the management platform 1200 may include a user verification module 1222 for verifying the identity and proper control by users. The locking mechanism 212 may be configured to remain locked until the user is verified via the user verification module 1222. In some embodiments, the user may be verified via the mobile application. In some embodiments, the user may be verified by one or more biometric indicators, such as facial recognition, fingerprint recognition, DNA matching, vein pattern recognition, voice recognition, or recognition via any other suitable biometric. For example, the user verification module 1222 may be configured to send an unlock signal to the locking mechanism 212 in response to matching a fingerprint of a user attempting to administer injection with a stored fingerprint of a verified user. In some embodiments, the verification system may include verification by two-factor authentication, such as requiring that a user attempting to administer rejection meet two or more requirements of inputting a password or PIN, such as via a smartphone or the wearable device 1204, matching one or more biometric indicators of a verified user, and/or any other suitable method of verifying a user attempting to use the injection device 100.

In some embodiments, the management platform 1200 may include a dashboard configured to provide visual information related to injection administration compliance and a dashboard module 1224 for configuring and/or controlling the dashboard. The dashboard may be configured based on one or both of a patient profile and a prescribed health care plan for a patient. The dashboard may be automatically populated with data from the injection device 100, such as the administration data 500. The dashboard may be configured to provide one or more alerts based on one or more events detected by the injection device 100, such as injection, fraud, pharmaceutical degradation, etc.

In some embodiments, the management platform 1200 may include a scheduling module 1226 for scheduling user actions related to injection administration. The scheduling module 1226 may be configured based on one or more of a patient profile, a profile for a specified injectable item, and a prescribed health care plan for a patient. The scheduling module 1226 may be configured based on events collected from the injection device 100.

In some embodiments, the management platform 1200 may include an artificial intelligence module 1228 capable of providing many machine learning, deep learning, and various artificial intelligence services. The artificial intelligence module 1228 may be configured to learn on a training set of data to train to determine and/or optimize the scheduling of future actions of a user, such as injection administration, medication intake, and/or general wellness habits. The artificial intelligence module 1228 may be configured based on one or more of a patient profile, a profile for a specific pharmaceutical, a profile for the injection device 100, and a prescribed health care plan for a patient.

In some embodiments, the artificial intelligence module 1228 may be configured and/or trained to determine that a detected user behavior may negatively impact a user's wellness or injection program. The artificial intelligence module 1228 may be configured to generate an alert to warn the user about the detected behavior. In some embodiments, the alerts module 1210 may be configured based on user behavior detected by the artificial intelligence module 1228 to deliver alerts based thereon.

In some embodiments, the artificial intelligence module 1228 may be configured and/or trained to determine whether the injection device 100 was fraudulently used or wasted. The artificial intelligence module 1228 may be configured and/or trained based on events collected from the injection device 100, such as the administration data 500.

In some embodiments, the artificial intelligence module 1228 may be configured and/or trained to generate a compliance score for an injection. The compliance score may be a quantitative or qualitative value related to one or more aspects of injection via the injection device 100, such as the administration data 500. The artificial intelligence module 1228 may be trailed to generate the compliance score from historical data from the injection device 100, such as the administration data 500.

The terms "a" or "an," as used herein, are defined as one or more than one. The term "another," as used herein, is defined as at least a second or more. The terms "including" and/or "having," as used herein, are defined as comprising (i.e., open transition).

While only a few embodiments of the present disclosure have been shown and described, it will be obvious to those skilled in the art that many changes and modifications may be made thereunto without departing from the spirit and scope of the present disclosure as described in the following claims. All patent applications and patents, both foreign and domestic, and all other publications referenced herein are incorporated herein in their entireties to the full extent permitted by law.

The methods and systems described herein may be deployed in part or in whole through a machine that executes computer software, program codes, and/or instructions on a processor. The present disclosure may be implemented as a method on the machine, as a system or apparatus as part of or in relation to the machine, or as a computer program product embodied in a computer-readable medium executing on one or more of the machines. In embodiments, the processor may be part of a server, cloud server, client, network infrastructure, mobile computing platform, stationary computing platform, or other computing platforms. A processor may be any kind of computational or processing device capable of executing program instructions, codes, binary instructions and the like. The processor may be or may include a signal processor, digital processor, embedded processor, microprocessor or any variant such as a co-processor (math co-processor, graphic co-processor, communication co-processor and the like) and the like that may directly or indirectly facilitate execution of program code or program instructions stored thereon. In addition, the processor may enable the execution of multiple programs, threads, and codes. The threads may be executed simultaneously to enhance the performance of the processor and to facilitate simultaneous operations of the application. By way of implementation, methods, program codes, program instructions and the like described herein may be implemented in one or more threads. The thread may spawn other threads that may have assigned priorities associated with them; the processor may execute these threads based on priority or any other order based on instructions provided in the program code. The processor, or any machine utilizing one, may include non-transitory memory that stores methods, codes, instructions and programs as described herein and elsewhere. The processor may access a non-transitory storage medium through an interface that may store methods, codes, and instructions as described herein and elsewhere. The storage medium associated with the processor for storing methods, programs, codes, program instructions or other type of instructions capable of being executed by the computing or processing device may include but may not be limited to one or more of a CD-ROM, DVD, memory, hard disk, flash drive, RAM, ROM, cache and the like.

A processor may include one or more cores that may enhance speed and performance of a multiprocessor. In embodiments, the process may be a dual-core processor, quad-core processors, other chip-level multiprocessors and the like that combine two or more independent cores (called a die).

The methods and systems described herein may be deployed in part or in whole through a machine that executes computer software on a server, client, firewall, gateway, hub, router, or other such computer and/or networking hardware. The software program may be associated with a server that may include a file server, print server, domain server, Internet server, intranet server, cloud server, and other variants such as a secondary server, host server, distributed server and the like. The server may include one or more of memories, processors, computer-readable media, storage media, ports (physical and virtual), communication devices, and interfaces capable of accessing other servers, clients, machines, and devices through a wired or a wireless medium, and the like. The methods, programs, or codes as described herein and elsewhere may be executed by the server. In addition, other devices required for the execution of methods as described in this application may be considered as a part of the infrastructure associated with the server.

The server may provide an interface to other devices including, without limitation, clients, other servers, printers, database servers, print servers, file servers, communication servers, distributed servers, social networks, and the like. Additionally, this coupling and/or connection may facilitate remote execution of programs across the network. The networking of some or all of these devices may facilitate parallel processing of a program or method at one or more locations without deviating from the scope of the disclosure. In addition, any of the devices attached to the server through an interface may include at least one storage medium capable of storing methods, programs, code and/or instructions. A central repository may provide program instructions to be executed on different devices. In this implementation, the remote repository may act as a storage medium for program code, instructions, and programs.

The software program may be associated with a client that may include a file client, print client, domain client, Internet client, intranet client and other variants such as secondary client, host client, distributed client and the like. The client may include one or more of memories, processors, computer-readable media, storage media, ports (physical and virtual), communication devices, and interfaces capable of accessing other clients, servers, machines, and devices through a wired or a wireless medium, and the like. The methods, programs, or codes as described herein and elsewhere may be executed by the client. In addition, other devices required for the execution of methods as described in this application may be considered as a part of the infrastructure associated with the client.

The client may provide an interface to other devices including, without limitation, servers, other clients, printers, database servers, print servers, file servers, communication servers, distributed servers and the like. Additionally, this coupling and/or connection may facilitate remote execution of programs across the network. The networking of some or all of these devices may facilitate parallel processing of a program or method at one or more locations without deviating from the scope of the disclosure. In addition, any of the devices attached to the client through an interface may include at least one storage medium capable of storing methods, programs, applications, code and/or instructions. A central repository may provide program instructions to be executed on different devices. In this implementation, the remote repository may act as a storage medium for program code, instructions, and programs.

The methods and systems described herein may be deployed in part or in whole through network infrastructures. The network infrastructure may include elements such as computing devices, servers, routers, hubs, firewalls, clients, personal computers, communication devices, routing devices and other active and passive devices, modules and/or components as known in the art. The computing and/or non-computing device(s) associated with the network infrastructure may include, apart from other components, a storage medium such as flash memory, buffer, stack, RAM, ROM and the like. The processes, methods, program codes, instructions described herein and elsewhere may be executed by one or more of the network infrastructural elements. The methods and systems described herein may be adapted for use with any kind of private, community, or hybrid cloud computing network or cloud computing environment, including those which involve features of software as a service (SaaS), platform as a service (PaaS), and/or infrastructure as a service (IaaS).

The methods, program codes, and instructions described herein and elsewhere may be implemented on a cellular network having multiple cells. The cellular network may either be frequency division multiple access (FDMA) network or code division multiple access (CDMA) network. The cellular network may include mobile devices, cell sites, base stations, repeaters, antennas, towers, and the like. The cell network may be a GSM, GPRS, 3G, 4G, 5G, EVDO, mesh, or other network types.

The methods, program codes, and instructions described herein and elsewhere may be implemented on or through mobile devices. The mobile devices may include navigation devices, cell phones, mobile phones, mobile personal digital assistants, laptops, palmtops, netbooks, pagers, electronic book readers, music players and the like. These devices may include, apart from other components, a storage medium such as a flash memory, buffer, RAM, ROM and one or more computing devices. The computing devices associated with mobile devices may be enabled to execute program codes, methods, and instructions stored thereon. Alternatively, the mobile devices may be configured to execute instructions in collaboration with other devices. The mobile devices may communicate with base stations interfaced with servers and configured to execute program codes. The mobile devices may communicate on a peer-to-peer network, mesh network, or other communications networks. The program code may be stored on the storage medium associated with the server and executed by a computing device embedded within the server. The base station may include a computing device and a storage medium. The storage device may store program codes and instructions executed by the computing devices associated with the base station.

The computer software, program codes, and/or instructions may be stored and/or accessed on machine readable media that may include: computer components, devices, and recording media that retain digital data used for computing for some interval of time; semiconductor storage known as random access memory (RAM); mass storage typically for more permanent storage, such as optical discs, forms of magnetic storage like hard disks, tapes, drums, cards and other types; processor registers, cache memory, volatile memory, non-volatile memory; optical storage such as CD, DVD; removable media such as flash memory (e.g., USB sticks or keys), floppy disks, magnetic tape, paper tape, punch cards, standalone RAM disks, Zip drives, removable mass storage, off-line, and the like; other computer memory such as dynamic memory, static memory, read/write storage, mutable storage, read only, random access, sequential access, location addressable, file addressable, content addressable, network attached storage, storage area network, bar codes, magnetic ink, and the like.

The methods and systems described herein may transform physical and/or intangible items from one state to another. The methods and systems described herein may also transform data representing physical and/or intangible items from one state to another.

The elements described and depicted herein, including in flowcharts and block diagrams throughout the figures, imply logical boundaries between the elements. However, according to software or hardware engineering practices, the depicted elements and the functions thereof may be implemented on machines through computer-executable media having a processor capable of executing program instructions stored thereon as a monolithic software structure, as standalone software modules, or as modules that employ external routines, code, services, and so forth, or any combination of these, and all such implementations may be within the scope of the present disclosure. Examples of such machines may include, but may not be limited to, personal digital assistants, laptops, personal computers, mobile phones, other handheld computing devices, medical equipment, wired or wireless communication devices, transducers, chips, calculators, satellites, tablet PCs, electronic books, gadgets, electronic devices, devices having artificial intelligence, computing devices, networking equipment, servers, routers and the like. Furthermore, the elements depicted in the flowchart and block diagrams or any other logical component may be implemented on a machine capable of executing program instructions. Thus, while the foregoing drawings and descriptions set forth functional aspects of the disclosed systems, no particular arrangement of software for implementing these functional aspects should be inferred from these descriptions unless explicitly stated or otherwise clear from the context. Similarly, it will be appreciated that the various steps identified and described above may be varied and that the order of steps may be adapted to particular applications of the techniques disclosed herein. All such variations and modifications are intended to fall within the scope of this disclosure. As such, the depiction and/or description of an order for various steps should not be understood to require a particular order of execution for those steps, unless required by a particular application, or explicitly stated or otherwise clear from the context.

The methods and/or processes described above, and steps associated therewith, may be realized in hardware, software or any combination of hardware and software suitable for a particular application. The hardware may include a general-purpose computer and/or dedicated computing device or specific computing device or particular aspect or component of a specific computing device. The processes may be realized in one or more microprocessors, microcontrollers, embedded microcontrollers, programmable digital signal processors or other programmable devices, along with internal and/or external memory. The processes may also, or instead, be embodied in an application-specific integrated circuit, a programmable gate array, programmable array logic, or any other device or combination of devices that may be configured to process electronic signals. It will further be appreciated that one or more of the processes may be realized as a computer executable code capable of being executed on a machine-readable medium. The computer-executable code may be created using a structured programming language such as C, an object-oriented programming language such as C++, or any other high-level or low-level programming language (including assembly languages, hardware description languages, and database programming languages and technologies) that may be stored, compiled or interpreted to run on one of the above devices, as well as heterogeneous combinations of processors, processor architectures, or combinations of different hardware and software, or any other machine capable of executing program instructions.

Thus, in one aspect, methods described above and combinations thereof may be embodied in computer-executable code that, when executing on one or more computing devices, performs the steps thereof. In another aspect, the methods may be embodied in systems that perform the steps thereof and may be distributed across devices in a number of ways, or all of the functionality may be integrated into a dedicated, standalone device or other hardware. In another aspect, the means for performing the steps associated with the processes described above may include any of the hardware and/or software described above. All such permutations and combinations are intended to fall within the scope of the present disclosure.

While the disclosure has been disclosed in connection with the preferred embodiments shown and described in detail, various modifications and improvements thereon will become readily apparent to those skilled in the art. Accordingly, the spirit and scope of the present disclosure is not to be limited by the foregoing examples but is to be understood in the broadest sense allowable by law.

The use of the terms "a" and "an" and "the" and similar referents in the context of describing the disclosure (especially in the context of the following claims) is to be construed to cover both the singular and the plural unless otherwise indicated herein or clearly contradicted by context. The terms "comprising," "having," "including," and "containing" are to be construed as open-ended terms (i.e., meaning "including, but not limited to,") unless otherwise noted. Recitations of ranges of values herein are merely intended to serve as a shorthand method of referring individually to each separate value falling within the range, unless otherwise indicated herein, and each separate value is incorporated into the specification as if it were individually recited herein. All methods described herein may be performed in any suitable order unless otherwise indicated herein or otherwise clearly contradicted by context. The use of any and all examples, or exemplary language (e.g., "such as") provided herein, is intended merely to better illuminate the disclosure and does not pose a limitation on the scope of the disclosure unless otherwise claimed. No language in the specification should be construed as indicating any non-claimed element as essential to the practice of the disclosure.

While the foregoing written description enables one skilled in the art to make and use what is considered presently to be the best mode thereof, those skilled in the art will understand and appreciate the existence of variations, combinations, and equivalents of the specific embodiment, method, and examples herein. The disclosure should therefore not be limited by the above-described embodiment, method, and examples, but by all embodiments and methods within the scope and spirit of the disclosure.

Any element in a claim that does not explicitly state "means for" performing a specified function, or "step for" performing a specified function, is not to be interpreted as a "means" or "step" clause as specified in 35 U.S.C. § 112(f). In particular, any use of "step of" in the claims is not intended to invoke the provision of 35 U.S.C. § 112(f).

Persons skilled in the art may appreciate that numerous design configurations may be possible to enjoy the functional benefits of the inventive systems. Thus, given the wide variety of configurations and arrangements of embodiments of the present disclosure the scope of the disclosure is reflected by the breadth of the claims below rather than narrowed by the embodiments described above.

What is claimed is:

1. An intelligent injection device for injection of a pharmaceutical into a patient, the intelligent injection device comprising:

- a barrel having an interior for holding a pharmaceutical, the barrel further having a first end and a second end;
- a needle in fluid communication with the barrel and connected with the first end of the barrel;
- a piston positioned within the second end of the barrel, the piston including a plunger having a fluid-tight interaction with the interior of the barrel;
- a mechanical switch disposed on the piston and configured to close upon completion of injection of said pharmaceutical into said patient;
- a wireless module configured to transmit administration data related to injection of said pharmaceutical from the intelligent injection device, wherein the wireless module is coupled to the intelligent injection device;
- a microprocessor in electrical communication with the mechanical switch and the wireless module, wherein the microprocessor is configured to transmit the administration data related to injection of said pharmaceutical via the wireless module in response to completion of the injection of said pharmaceutical into said patient resulting in closing of the mechanical switch;
- a temperature sensor in electrical communication with the microprocessor and configured to sense a temperature of said pharmaceutical and transmit temperature data to the microprocessor indicative of the temperature of said pharmaceutical; and
- a locking mechanism engaged with the piston and in electrical communication with the microprocessor, wherein the microprocessor is configured to transmit a locking signal to the locking mechanism, and the locking mechanism is configured to lock the piston in response to receiving the locking signal in response to a degradation risk, determined by the microprocessor, correlating to said pharmaceutical being above a predetermined threshold.

2. The intelligent injection device of claim 1, further comprising a load sensor in electrical communication with the microprocessor and configured to sense force caused by depression of the plunger and transmit force data to the microprocessor indicative of the force caused by the depression of the plunger.

3. The intelligent injection device of claim 1, further comprising an amount sensor in electrical communication with the microprocessor and configured to sense an amount of said pharmaceutical injected into said patient upon depression of the plunger and transmit pharmaceutical amount data to the microprocessor indicative of said amount of said pharmaceutical injected into said patient upon the depression of the plunger.

4. The intelligent injection device of claim 1, further comprising a damage sensor in electrical communication with the microprocessor and configured to sense damage to the intelligent injection device and transmit damage data to the microprocessor indicative of the damage to the intelligent injection device.

5. The intelligent injection device of claim 1, further comprising an automatic injection system configured to facilitate automatic delivery of said pharmaceutical by the intelligent injection device into said patient.

6. The intelligent injection device of claim 1, further comprising an injectable administration compliance management platform configured to operate an Internet of Things-based system at least partially implemented in the microprocessor of the intelligent injection device.

7. The intelligent injection device of claim 6, wherein the injectable administration compliance management platform is configured for real-time monitoring of the intelligent injection device and management of adherence to an injectable administration plan.

8. The intelligent injection device of claim 1, further comprising an injectable administration compliance management platform configured to receive data collected by at least one Internet of Things device and combine with data collected by the intelligent injection device.

9. The intelligent injection device of claim 1, further comprising an injectable administration compliance management platform configured to receive data collected by at least one Internet of Things device and at least one wearable device and combine with data collected by the intelligent injection device.

10. The intelligent injection device of claim 1, further comprising an injectable administration compliance management platform configured to receive medical compliance data and combine with data collected by the intelligent injection device.

11. The intelligent injection device of claim 1, further comprising an injectable administration compliance management platform configured to receive at least one of an artificial intelligence datum, artificial intelligence model or machine learning model and combine with data collected by the intelligent injection device.

12. The intelligent injection device of claim 1, further comprising an injectable administration compliance management platform configured to receive at least one of electronic medical record data or emergency health record data and combine with data collected by the intelligent injection device.

13. The intelligent injection device of claim 1, further comprising an injectable administration compliance management platform configured to operate an intelligent virtual care assistant module to perform a task for a person associated with a usage of the intelligent injection device.

14. The intelligent injection device of claim 13, wherein the intelligent virtual care assistant module displays an alert to the person associated with the usage of the intelligent injection device.

15. The intelligent injection device of claim 13, wherein the intelligent virtual care assistant module is configured to present a virtual reality display to the person using the intelligent injection device.

16. The intelligent injection device of claim 13, wherein the intelligent virtual care assistant module is configured to present an augmented reality display to one of the person and the patient using the intelligent injection device.

* * * * *